United States Patent
Schaefer et al.

[11] Patent Number: 6,165,941
[45] Date of Patent: Dec. 26, 2000

[54] SUBSTITUTED 2-PHENYLPYRIDINES

[75] Inventors: Peter Schaefer, Ottersheim; Gerhard Hamprecht, Weinheim; Elisabeth Heistracher, Ludwigshafen; Hartmann Koenig, Limburgerhof; Ralf Klintz, Gruenstadt; Peter Muenster, Neulussheim; Harald Rang, Altrip; Karl-Otto Westphalen, Speyer; Matthias Gerber, Limburgerhof; Helmut Walter, Obrigheim, all of Germany

[73] Assignee: BASF Aktiengesellschaft, Ludwigshafen, Germany

[21] Appl. No.: 08/592,354

[22] PCT Filed: Jul. 11, 1994

[86] PCT No.: PCT/EP94/02264

§ 371 Date: Jan. 11, 1996

§ 102(e) Date: Jan. 11, 1996

[87] PCT Pub. No.: WO95/02590

PCT Pub. Date: Jan. 26, 1995

[30] Foreign Application Priority Data

Jul. 16, 1993 [DE] Germany .............................. 43 23 916

[51] Int. Cl.$^7$ .......................... A01N 43/84; C07D 265/36
[52] U.S. Cl. ............................. 504/225; 544/73; 544/105
[58] Field of Search ...................... 544/105, 73; 504/225

[56] References Cited

FOREIGN PATENT DOCUMENTS

| | | |
|---|---|---|
| 2039770 | 10/1991 | Canada . |
| 2078469 | 3/1993 | Canada . |
| 067 511 | 12/1982 | European Pat. Off. . |
| 167 491 | 1/1986 | European Pat. Off. . |
| 263 958 | 4/1988 | European Pat. Off. . |
| 412 681 | 2/1991 | European Pat. Off. . |
| 420194 | 4/1991 | European Pat. Off. . |
| 434 440 | 6/1991 | European Pat. Off. . |
| 448 206 | 9/1991 | European Pat. Off. . |
| 476 697 | 3/1992 | European Pat. Off. . |
| 479420 | 4/1992 | European Pat. Off. . |
| 508800 | 10/1992 | European Pat. Off. . |
| 4020257 | 1/1992 | Germany . |
| 92/22203 | 12/1992 | WIPO . |
| 94/05153 | 3/1994 | WIPO . |
| 94/10118 | 5/1994 | WIPO . |

OTHER PUBLICATIONS

Katagiri et al., *Chem. Pharm Bull*, vol., 36, No. 9, pp. 3354–3372, 1988.
Chem Abst., vol. 113, No. 190, 171837j, Nippon Kagaku Kaishi 5, 466–471 (English abstract of JP 1211586), 1988.
Boy et al., *Synlet*, vol. 12, p. 923, Dec. 1991.
Pesticide Science, vol. 21, 1987, pp. 175–179.
Chem. Abst., vol. 114, No. 11, 96724k, Izv. Timiryazevsk.S–Kh. Akad. 3, pp. 155–160, 1990.

*Primary Examiner*—Mukund J. Shah
*Assistant Examiner*—Brenda Coleman
*Attorney, Agent, or Firm*—Keil & Weinkauf

[57] ABSTRACT

A substituted 2-phenylpyridine of the formula I

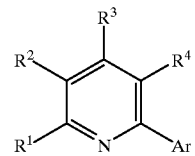

(I)

where Ar is

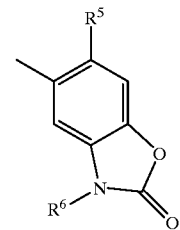

(a)

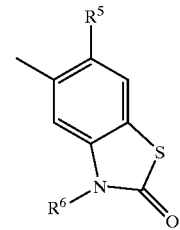

(b)

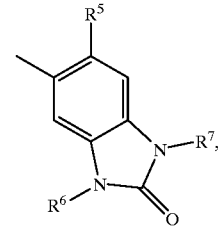

(c)

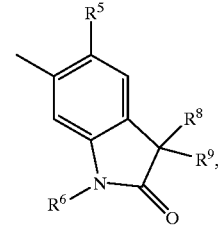

(d)

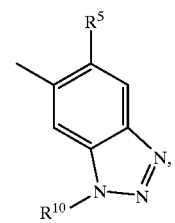

(e)

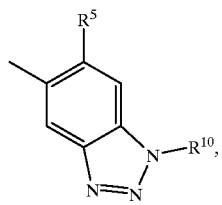 (f)
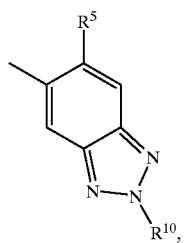 (g)
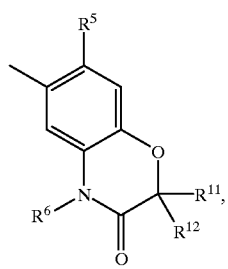 (h)
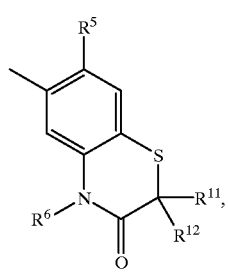 (i)
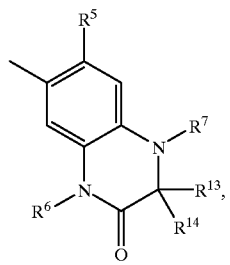 (k)
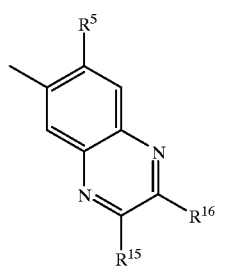 (l)
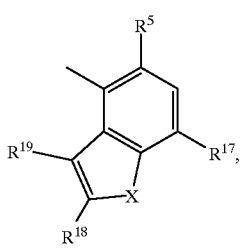 (m)
and the N-oxides of I and the agriculturally utilizable salts of I where these exist. Use: herbicides; desiccation/defoliation of plants.
6 Claims, No Drawings

SUBSTITUTED 2-PHENYLPYRIDINES

This is a National Stage Application under 35 U.S.C. §371, based on International Application No. PCT/EP 94/02,264, filed on Jul. 11, 1994.

The present invention relates to novel substituted 2-phenylpyridines of the formula I

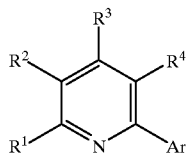

I where the substituents have the following meanings:

$R^1$, $R^3$ and $R^4$ independently of one another are hydrogen, halogen, $C_1$-$C_4$-alkyl, $C_1$-$C_4$-haloalkyl, $C_1$-$C_4$-alkoxy-$C_1$-$C_4$-alkyl, $C_1$-$C_4$-alkoxy, $C_1$-$C_4$-alkoxy-$C_1$-$C_4$-alkoxy, hydroxyl, $C_1$-$C_4$-haloalkoxy, ($C_1$-$C_5$-alkyl)-carbonyloxy, ($C_1$-$C_5$-haloalkyl)carbonyloxy, SH, $C_1$-$C_4$-alkylthio, $C_1$-$C_4$-alkylsulfinyl, $C_1$-$C_4$-alkylsulfonyl, $C_1$-$C_4$-haloalkylthio, $C_1$-$C_4$-haloalkylsulfinyl, $C_1$-$C_4$-haloalkylsulfonyl, formyl, cyano, hydroxycarbonyl, ($C_1$-$C_4$-alkoxy)carbonyl, $C_1$-$C_4$-alkoxy-($C_1$-$C_4$-alkoxy)carbonyl, ($C_1$-$C_4$-haloalkoxy)-carbonyl, ($C_1$-$C_4$-alkyl)carbonyl, ($C_1$-$C_4$-haloalkyl)carbonyl, $C_1$-$C_4$-alkoxy-($C_1$-$C_4$-alkyl)carbonyl, $CONH_2$, ($C_1$-$C_4$-alkyl)amino-carbonyl, di($C_1$-$C_4$-alkyl)aminocarbonyl, pyrrolidinylcarbonyl, piperidinylcarbonyl, morpholinylcarbonyl, nitro, amino, $C_1$-$C_4$-alkylamino, di($C_1$-$C_4$-alkyl)amino, pyrrolidinyl, piperidinyl, morpholinyl, ($C_1$-$C_4$-alkyl)carbonylamino, ($C_1$-$C_4$-haloalkyl)carbonylamino or $C_1$-$C_4$-alkylsulfonylamino;

$R^2$ is halogen, cyano, nitro, $C_1$-$C_4$-alkyl, $C_1$-$C_4$-haloalkyl, $C_1$-$C_4$-alkoxy, $C_1$-$C_4$-haloalkoxy, $C_1$-$C_4$-alkylthio, $C_1$-$C_4$-haloalkylthio or together with $R^1$ or with $R^3$ is a trimethylene or tetramethylene chain;

Ar is a radical

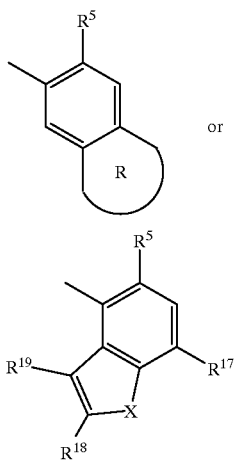

where
$R^5$ is hydrogen or halogen;
X is oxygen or sulfur;
$R^{17}$ is halogen, cyano, nitro, hydroxyl, $C_1$-$C_4$-alkoxy or trifluormethyl;
$R^{18}$ is hydrogen, $C_1$-$C_6$-alkyl, $C_1$-$C_6$-haloalkyl or $C_1$-$C_4$-alkoxy-$C_1$-$C_4$-alkyl and $R^{19}$ is hydrogen or $C_1$-$C_6$-alkyl and where the ring R is a fused heterocyclic ring which, together with the phenyl ring, forms one of the following bicyclic rings (a) to (1):

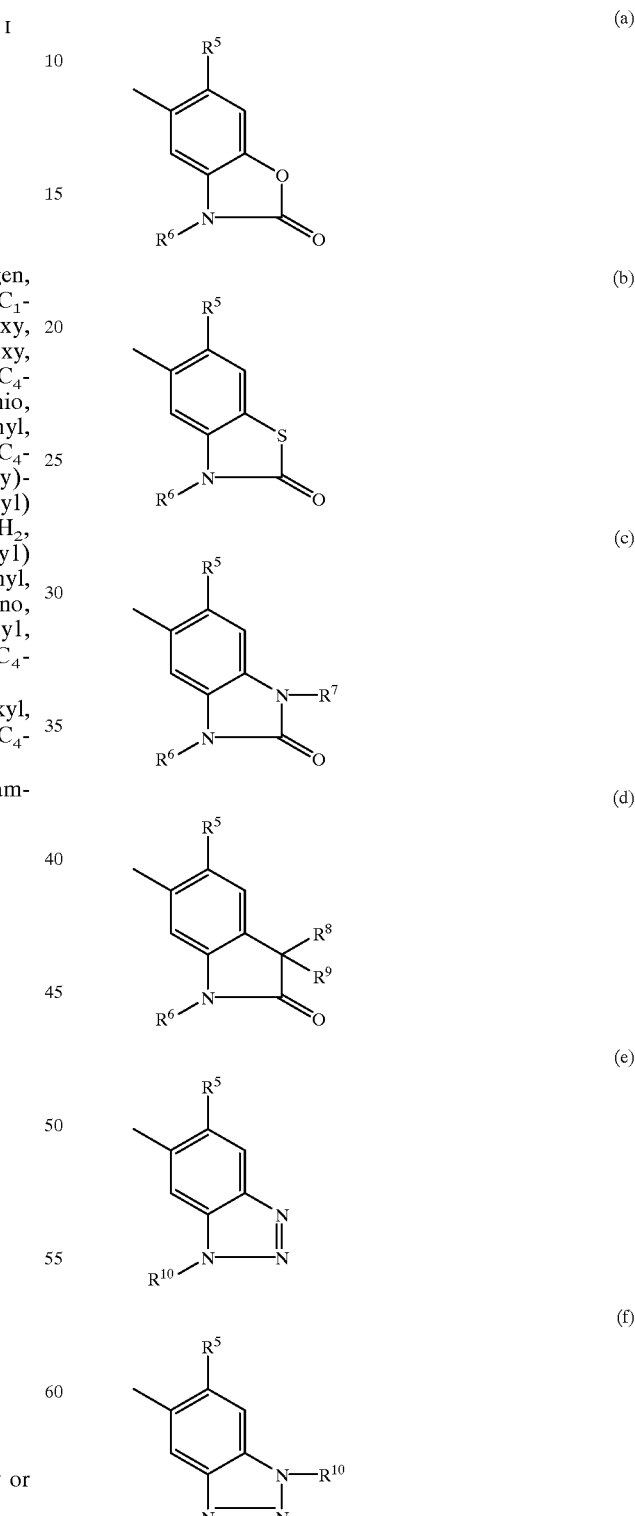

-continued (g)
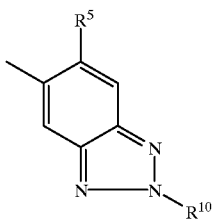

(h)
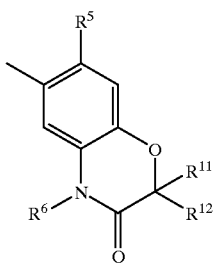

(i)
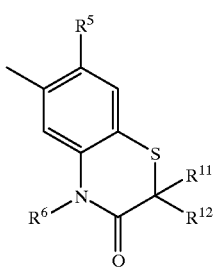

(k)
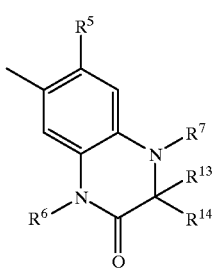

(l)
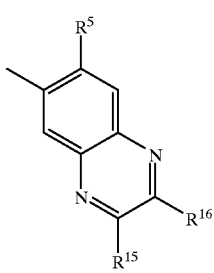

$R^6$, $R^7$ and $R^{10}$ independently of one another are hydrogen, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_1$-$C_4$-alkoxy-$C_1$-$C_4$-alkyl, $C_1$-$C_4$-alkoxy-$C_1$-$C_2$-alkoxy-$C_1$-$C_4$-alkyl, 1-phenylpropen-3-yl, cyano-$C_1$-$C_4$-alkyl, $C_3$-$C_6$-cycloalkyl-$C_1$-$C_6$-alkyl, (1-methylthiocycloprop-1-yl)-methyl, carboxyl-$C_1$-$C_4$-alkyl, ($C_1$-$C_6$-alkoxy)carbonyl-$C_1$-$C_4$-alkyl, ($C_1$-$C_6$-haloalkoxy)carbonyl-$C_1$-$C_4$-alkyl, $C_1$-$C_4$-alkoxy-($C_1$-$C_2$-alkoxy)carbonyl-$C_1$-$C_4$-alkyl, ($C_1$-$C_6$-alkoxy)carbonyl-($C_1$-$C_2$-alkoxy)carbonyl-$C_1$-$C_4$-alkyl, $C_3$-$C_6$-cycloalkyl-($C_1$-$C_2$-alkoxy)carbonyl-$C_1$-$C_4$-alkyl, $C_1$-$C_5$-alkyl-aminocarbonyl-$C_1$-$C_4$-alkyl, di-($C_1$-$C_5$-alkyl) aminocarbonyl-$C_1$-$C_4$-alkyl, $C_3$-$C_6$-cycloalkyl, $C_1$-$C_4$-alkylthio-$C_1$-$C_4$-alkyl, $C_1$-$C_4$-alkylsulfonyl, $C_3$-$C_6$-alkenyloxy-$C_1$-$C_4$-alkyl, $C_1$-$C_8$-alkylcarbonyl, $C_1$-$C_8$-alkoxycarbonyl, $C_1$-$C_6$-alkoxy, oxetan-3-yl-oxycarbonyl-$C_1$-$C_4$-alkyl, thietan-3-yl-oxycarbonyl-$C_1$-$C_4$-alkyl, oxetan-3-ylmethyl, 3-($C_1$-$C_4$-alkyl)-oxetan-3-ylmethyl or benzyl, which can be unsubstituted or can carry one to three radicals selected from the group consisting of halogen, $C_1$-$C_4$-alkyl and $C_1$-$C_4$-alkoxy;

$R^8$ and $R^9$ independently of one another are hydrogen, $C_1$-$C_4$-alkyl, hydroxycarbonyl, ($C_1$-$C_4$-alkoxy)carbonyl or together are ethylene, propylene, butylene, pentylene or hexylene;

$R^{11}$, $R^{12}$, $R^{13}$ and $R^{14}$ independently of one another are hydrogen, halogen, $C_1$-$C_6$-alkyl, $C_1$-$C_6$-haloalkyl or $C_1$-$C_4$-alkoxy-$C_1$-$C_4$-alkyl;

$R^{15}$ and $R^{16}$ independently of one another are hydrogen, chlorine, bromine, $C_1$-$C_8$-alkyl, —$OR^{20}$, —$SR^{21}$ or —$N(R^{22})$—$R^{23}$;

$R^{20}$ and $R^{21}$ independently of one another are hydrogen, $C_1$-$C_8$-alkyl, $C_1$-$C_8$-haloalkyl, $C_4$-$C_7$-cycloalkyl, which for its part can carry up to three $C_1$-$C_3$-alkyl radicals, $C_3$-$C_6$-alkenyl, $C_5$-$C_7$-cycloalkenyl, which for its part can carry up to three $C_1$-$C_3$-alkyl radicals, $C_3$-$C_6$-haloalkenyl, cyano-$C_1$-$C_8$-alkyl, $C_3$-$C_6$-alkynyl, $C_1$-$C_4$-alkoxy-$C_1$-$C_4$-alkyl, 2-tetrahydrofuranyl-$C_1$-$C_8$-alkyl, 3-oxetanyl, 3-thietanyl, carboxyl-$C_1$-$C_6$-alkyl, ($C_1$-$C_8$-alkoxy)carbonyl-$C_1$-$C_6$-alkyl, ($C_1$-$C_6$-alkoxy)carbonyl-($C_3$-$C_7$-cycloalkyl), $C_1$-$C_4$-alkoxy-($C_1$-$C_4$-alkoxy)carbonyl-$C_1$-$C_6$-alkyl, cyclopropylmethyl, (1-methylthiocyclo-prop-1-yl)methyl, —CH(SH)—COOH, —CH(SH)—CO—($C_1$-$C_8$-alkoxy), —CH($C_1$-$C_8$-alkylthio)—COOH, —CH($C_1$-$C_4$-alkylthio)—CO—($C_1$-$C_8$-alkoxy), —$CH_2$—CO—N($R^9$)—$R^{10}$, —CH($C_1$-$C_4$-alkyl)—CO—N($R^9$)—$R^{10}$, —C($C_1$-$C_4$-alkyl)$_2$—CO—N($R^9$)—$R^{10}$, —$CH_2$—CO—N($R^9$)—$SO_2$—($C_1$-$C_4$-alkyl), —CH($C_1$-$C_4$-alkyl)—CO—N($R^9$)—$SO_2$—($C_1$-$C_4$-alkyl), —C($C_1$-$C_4$-alkyl)$_2$—CO—N($R^9$)—$SO_2$—($C_1$-$C_4$-alkyl), —S—CO—$NH_2$, —S—CO—N($C_1$-$C_4$-alkyl)-($C_1$-$C_4$-alkyl), —$CH_2$—CO—O—($C_1$-$C_6$-alkylene)—COOH, —$CH_2$—CO—O—($C_1$-$C_6$-alkylene)—CO—($C_1$-$C_6$-alkoxy), —C($C_1$-$C_4$-alkyl)$_2$—CO—O—($C_1$-$C_6$-alkylene)—COOH, —C($C_1$-$C_4$-alkyl)$_2$—CO—O—($C_1$-$C_4$-alkylene)—CO—($C_1$-$C_6$-alkoxy), —CH($C_1$-$C_4$-alkyl)—CO—O—($C_1$-$C_6$-alkylene)—COOH, —CH($C_1$-$C_4$-alkyl)—CO—O—($C_1$-$C_6$-alkylene)—CO—($C_1$-$C_6$-alkoxy), $C_3$-$C_9$-($\alpha$-alkylalkylidene)iminooxy-$C_1$-$C_6$-alkyl, phenyl, phenyl-$C_1$-$C_6$-alkyl, phenyl-$C_3$-$C_6$-alkenyl, phenyl-$C_3$-$C_6$-alkynyl or phenoxy-$C_1$-$C_6$-alkyl, where the phenyl ring in each case can be unsubstituted or can carry one to three radicals selected from the group consisting of halogen, nitro, cyano, $C_1$-$C_4$-alkyl, $C_1$-$C_4$-alkoxy, $C_1$-$C_4$-alkylthio, $C_1$-$C_4$-haloalkyl and $C_2$-$C_6$-alkenyl, 5- or 6-membered heteroaryl, heteroaryl-$C_1$-$C_6$-alkyl, heteroaryl-$C_3$-$C_6$-alkenyl, heteroaryl-$C_3$-$C_6$-alkynyl or heteroaryloxy-$C_1$-$C_6$-alkyl, where the heteroaromatic in each case contains one to three hetero atoms selected from a group consisting of one or two nitrogen atoms and an oxygen or sulfur atom, and where the heteroaromatic if desired can additionally carry on each substitutable ring atom a radical selected from the group consisting of hydroxyl, halogen, $C_1$-$C_4$-alkyl, $C_1$-$C_4$-alkoxy, $C_1$-$C_4$-alkylthio and $C_1$-$C_4$-haloalkyl;

$R^{22}$ and $R^{23}$ independently of one another are hydrogen, $C_1$-$C_8$-alkyl, $C_2$-$C_8$-alkenyl, $C_3$-$C_8$-alkynyl, $C_1$-$C_8$-haloalkyl, $C_1$-$C_4$-alkoxy-$C_1$-$C_4$-alkyl, $C_1$-$C_4$-alkylthio-$C_1$-$C_4$-alkyl, cyano-$C_1$-$C_8$-alkyl, carboxyl-$C_1$-$C_4$-alkyl, ($C_1$-$C_4$-alkoxy)carbonyl-$C_1$-$C_4$-alkyl, ($C_1$-$C_6$-alkoxy) carbonyl-($C_3$-$C_7$-cycloalkyl), $C_1$-$C_4$-alkylsulfonyl-$C_1$-$C_4$- alkyl, $C_3$-$C_8$-cycloalkyl, $C_1$-$C_6$-alkoxy, ($C_3$-$C_6$-cycloalkoxy)-carbonyl-$C_1$-$C_4$-alkyl, $C_1$-$C_4$-alkoxy-($C_1$-$C_4$-alkoxy)carbonyl-$C_1$-$C_4$-alkyl, phenyl, phenyl-$C_1$-$C_4$-alkyl, where the phenyl ring in each case can be unsubstituted or can carry one to three radicals selected from the group consisting of halogen, nitro, cyano, $C_1$-$C_4$-alkyl, $C_1$-$C_4$-alkoxy, $C_1$-$C_4$-alkylthio, $C_1$-$C_4$-haloalkyl and $C_2$-$C_6$-alkenyl, 5- or 6-membered heteroaryl or heteroaryl-$C_1$-$C_4$-alkyl, where the heteroaromatic contains one to three hetero atoms selected from a group consisting of one or two nitrogen atoms and an oxygen or sulfur atom, and where the heteroaromatic if desired can additionally carry on each substitutable ring atom a radical selected from the group consisting of hydroxyl, halogen, $C_1$-$C_4$-alkyl, $C_1$-$C_4$-alkoxy, $C_1$-$C_4$-alkylthio and $C_1$-$C_4$-haloalkyl;

and the N-oxides of I and the agriculturally utilizable salts of I if these exist.

In addition the invention relates to the use of compounds I, their N-oxides and/or agriculturally utilizable salts as herbicides and for the desiccation and/or defoliation of plants, herbicidal compositions and compositions for the desiccation and/or defoliation of plants, which contain the compounds I, their N-oxides and/or agriculturally utilizable salts as active substances, processes for preparing these herbicidal compositions and compositions for the desiccation and/or defoliation of plants, processes for controlling undesired plant growth and for the desiccation and/or defoliation of plants using the compounds I, and also using the N-oxides and the agriculturally utilizable salts of I, and also processes for preparing the compounds I.

The invention additionally relates to the use of phenylpyridines of the formula IV

IV

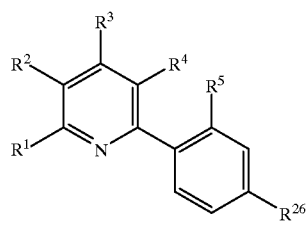

where the substituents $R^1$ and $R^5$ have the same meanings as in the compounds I and $R^{26}$ is fluorine, hydroxyl or $C_1$-$C_6$-alkoxy, and of aromatic boronic acids and boronic acid esters XIX and to novel 2-(4-hydroxy-5-nitrophenyl)pyridines IX, 2-(4-hydroxy-5-aminophenyl)pyridines X and carboxanilides XII.

2-Phenylpyridines have hitherto been disclosed in the following publications: EP-A 167 491; EP-A 412 681; WO 94/05153; WO 92/10118; WO 92/22203; CA 114(11), 96724k: Izv. Timiryazevsk.S-Kh. Akad. 3, 155–160; Pestic. Sci. 21(3), 175–179; CA 113(19), 171837j: Nippon Kagaku Kaishi 5, 466–471; JP 12 11586.

P. Boy et al. (Synlett 12, 923) describe the preparation of 4-[(trifluoromethyl)pyridyl]phenols:

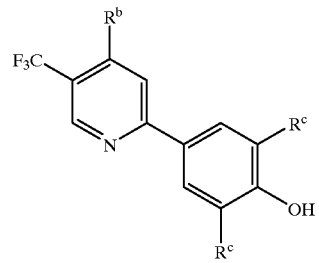

$R^b$=hydrogen or trifluoromethyl, $R^c$=hydrogen or tert-butyl.

N. Katagiri et al. (Chem. Pharm. Bull. 36 (9), 3354–72) describe the preparation of substituted 2-phenylpyridines:

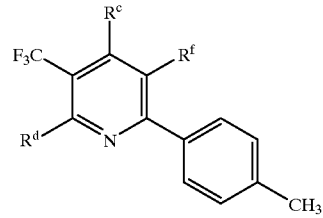

where $R^d$ is hydrogen, chlorine or methoxy, $R^e$ is hydrogen, methyl, ethyl or ethoxy and $R^f$ is hydrogen or methyl or $R^e$ and $R^f$ together are $(CH_2)_3$ or $(CH_2)_4$.

Finally, 2,6-diarylpyridine derivatives having herbicidal and defoliating properties have been disclosed in DE-A 40 20 257:

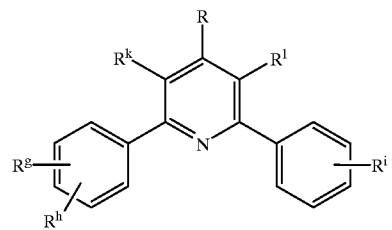

where $R^g$ and $R^h$ are hydrogen, halogen, alkyl, alkoxy or haloalkyl, $R^i$ is hydrogen, halogen, cyano, alkyl, alkoxy or haloalkyl and $R^k$ and $R^l$ are hydrogen or alkyl.

If the known compounds have a herbicidal or desiccant/defoliant action at all, they are not always completely satisfactory.

It was an object of the present invention to provide novel, in particular herbicidally active, compounds with which undesired plants can specifically be controlled better than previously.

We have now found the present substituted 2-phenylpyridines of the formula I. Herbicidal compositions have also been found which contain the compounds I and have a good herbicidal action. They are tolerable or selective, particularly in gramineous crops such as wheat, maize and rice.

Novel intermediates of the formulae IX, X and XII for preparing the substituted 2-phenylpyridines I have additionally been found.

The compounds I according to the invention are additionally suitable for the defoliation and desiccation of parts of plants for eg. cotton, potato, rape, sunflower, soybean or field beans.

The organic molecular moieties mentioned above for the substituents $R^1$ to $R^{27}$ or as radicals of (hetero)aromatics are, like the meaning halogen, collective terms for individual lists of the individual group members. All hydrocarbon chains, ie. all alkyl, alkenyl, alkynyl, haloalkyl, haloalkenyl, haloalkynyl and haloalkoxy moieties, and the α-alkylalkylidene moiety, can be straight-chain or branched. Halogenated substituents preferably carry one to five identical or different halogen atoms.

Specific examples of the moieties are halogen: fluorine, chlorine, bromine and iodine, preferably fluorine and chlorine;

$C_1$-$C_4$-alkyl: methyl, ethyl, n-propyl, 1-methylethyl, n-butyl, 1-methylpropyl, 2-methylpropyl and 1,1-dimethylethyl;

$C_1$-$C_6$-alkyl: $C_1$-$C_4$-alkyl as mentioned above, and also n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

$C_1$-$C_8$-alkyl: $C_1$-$C_6$-alkyl as mentioned above, and also, inter alia, n-heptyl, n-octyl;

$C_2$-$C_4$-alkenyl: ethenyl, prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl and 2-methylprop-2-en-1-yl;

$C_{3-C6}$-alkenyl: prop-1-en-1-yl, prop-2-en-1-yl, 1-methylethenyl, n-buten-1-yl, n-buten-2-yl, n-buten-3-yl, 1-methylprop-1-en-1-yl, 2-methylprop-1-en-1-yl, 1-methylprop-2-en-1-yl, 2-methylprop-2-en-1-yl, n-penten-1-yl, n-penten-2-yl, n-penten-3-yl, n-penten-4-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-2-yl, 1-ethylprop-2-en-1-yl, n-hex-1-en-1-yl, n-hex-2-en-1-yl, n-hex-3-en-1-yl, n-hex-4-en-1-yl, n-hex-5-en-1-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethylbut-2-en-1-yl, 2-ethylbut-3-en-1-yl, 1,1,2-trimethylprop-2-en-1-yl, 1-ethyl-1-methylprop-2-en-1-yl, 1-ethyl-2-methyl-prop-1-en-1-yl and 1-ethyl-2-methyl-prop-2-en-1-yl, preferably ethenyl and prop-2-en-1-yl;

$C_{2-C8}$-alkenyl: ethenyl, $C_3$–$C_6$-alkenyl as mentioned above, and, inter alia, n-hept-1-en-1-yl, n-hept-2-en-1-yl, n-hept-3-en-1-yl, n-hept-4-en-1-yl, n-hept-5-en-1-yl, n-hept-6-en-1-yl, n-oct-1-en-1-yl, n-oct-2-en-1-yl, n-oct-3-en-1-yl, n-oct-4-en-1-yl, n-oct-5-en-1-yl, n-oct-6-en-1-yl and n-oct-7-en-1-yl;

$C_2$–$C_6$-alkynyl: ethynyl and $C_{3-C6}$-alkynyl such as prop-1-yn-1-yl, prop-2-yn-3-yl, n-but-1-yn-1-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-1-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methylpent-2-yn-5-yl, preferably prop-2-yn-1-yl and 1-methylprop-2-yn-1-yl;

$C_2$–$C_8$-alkynyl: ethynyl, $C_3$–$C_6$-alkynyl as mentioned above, and, inter alia, n-hept-1-yn-1-yl, n-hept-2-yn-1-yl, n-hept-3-yn-1-yl, n-hept-4-yn-1-yl, n-hept-5-yn-1-yl, n-hept-6-yn-1-yl, n-oct-1-yn-1-yl, n-oct=2-yn-1-yl, n-oct-3-yn-1-yl, n-oct-4-yn-1-yl, n-oct-5-yn-1-yl, n-oct-6-yn-1-yl and n-oct-7-yn-1-yl;

$C_3$–$C_6$-haloalkenyl: $C_3$–$C_6$-alkenyl as mentioned above, where in each case one to three hydrogen atoms are replaced by fluorine, chlorine and/or bromine;

$C_2$–$C_8$-haloalkenyl: $C_2$–$C_8$-alkenyl as mentioned above, where in each case one to three hydrogen atoms are replaced by fluorine, chlorine and/or bromine;

$C_2$–$C_8$-haloalkynyl: $C_2$–$C_8$-alkynyl as mentioned above, where in each case one to three hydrogen atoms are replaced by fluorine, chlorine and/or bromine;

$C_2$–$C_8$-haloalkynyl: $C_2$–$C_8$-alkynyl as mentioned above, where in each case one to three hydrogen atoms are replaced by fluorine, chlorine and/or bromine;

$C_3$–$C_6$-cycloalkyl: cyclopropyl, cyclobutyl, cyclopentyl and cyclohexyl, preferably cyclopropyl, cyclopentyl and cyclohexyl;

$C_4$–$C_7$-cycloalkyl: cyclobutyl, cyclopentyl, cyclohexyl and cycloheptyl, preferably cyclopentyl and cyclohexyl;

$C_5$–$C_7$-cycloalkenyl eg.: cyclopent-1-enyl, cyclopent-2-enyl, cyclopent-3-enyl, cyclohex-1-enyl, cyclohex-2-enyl, cyclohex-3-enyl, cyclohept-1-enyl, cyclohept-2-enyl, cyclohept-3-enyl and cyclohept-4-enyl;

($C_3$–$C_6$-cycloalkoxy)carbonyl: cyclopropoxycarbonyl, cyclobutoxycarbonyl, cyclopentoxycarbonyl and cyclohexoxycarbonyl, preferably cyclopropoxycarbonyl, cyclopentoxycarbonyl and cyclohexoxycarbonyl;

$C_1$–$C_4$-haloalkyl: $C_1$–$C_4$-alkyl as mentioned above, which is partially or completely substituted by fluorine, chlorine and/or bromine, that is eg. chloromethyl, dichloromethyl, trichloromethyl, fluoromethyl, difluoromethyl, trifluoromethyl, chlorofluoromethyl, dichlorofluoromethyl, chlorodifluoromethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 3-chloropropyl, preferably trifluoromethyl;

$C_1$–$C_6$-haloalkyl: $C_1$–$C_6$-alkyl as mentioned above, which is partially or completely substituted by fluorine, chlorine and/or bromine;

$C_1–C_8$-haloalkyl: $C_1–C_8$-alkyl as mentioned above, which is partially or completely substituted by fluorine, chlorine and/or bromine, that is eg. the abovementioned $C_1–C_4$-haloalkyls;

cyano-$C_1–C_8$-alkyl: $C_1–C_8$-alkyl as mentioned above, whee in each case one hydrogen atom is replaced by the cyano group, that is eg. cyanomethyl, 1-cyanoeth-1-yl, 2-cyanoeth-1-yl, 1-cyanoprop-1-yl, 2-cyanoprop-1-yl, 3-cyanoprop-1-yl, 1-cyanoprop-2-yl, 2-cyanoprop-2-yl, 1-cyanobut-1-yl, 2-cyanobut-1-yl, 3-cyanobut-1-yl, 4-cyanobut-1-yl, 1-cyanobut-2-yl, 2-cyanobut-2-yl, 1-cyanobut-3-yl, 2-cyanobut-3-yl, 1-cyano-2-methylprop-3-yl, 2-cyano-2-methylprop-3-yl, 3-cyano-2-methylprop-3-yl, and 2-cyanomethylprop-2-yl, preferably cyanomethyl and 1-cyano-1-methylethyl;

phenyl-$C_1–C_4$-alkyl: $C_1–C_4$-alkyl as mentioned above, where in each case one hydrogen atom is replaced by the phenyl group, that is eg. benzyl, 1-phenylethyl, 2-phenylethyl, 1-phenylprop-1-yl, 2-phenylprop-1-yl, 3-phenylprop-1-yl, 1-phenylbut-1-yl, 2-phenylbut-1-yl, 3-phenylbut-1-yl, 4-phenylbut-1-yl, 1-phenylbut-2-yl, 2-phenylbut-2-yl, 3-phenylbut-2-yl, 3-phenylbut-2-yl, 4-phenylbut-2-yl, 1-(phenylmethyl)-eth-1-yl, 1-(phenylmethyl)-1-(methyl)eth-1-yl and 1-(phenylmethyl)prop-1-yl, preferably benzyl;

phenyl-$C_1–C_6$-alkyl: $C_1–C_6$-alkyl as mentioned above, where in each case one hydrogen atom is replaced by the phenyl group, that is eg. the abovementioned phenyl-$C_1–C_4$-alkyls;

phenyl-$C_3–C_6$-alkenyl: $C_3–C_6$-alkenyl as mentioned above, where one hydrogen atom in each case is replaced by the phenyl group;

phenyl-$C_3$-$C_6$-alkynyl: $C_3$-$C_6$-alkynyl as mentioned above, where one hydrogen atom in each case is replaced by the phenyl group;

$C_1–C_4$-alkoxy: methoxy, ethoxy, n-propoxy, 1-methylethoxy, n-butoxy, 1-methylpropoxy, 2-methylpropoxy and 1,1-dimethylethoxy, preferably methoxy, ethoxy and 1-methylethoxy;

$C_1–C_6$-alkoxy: $C_1–C_4$-alkoxy as mentioned above, and also n-pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, n-hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1–C_8$-alkoxy: $C_1–C_6$-alkoxy as mentioned above and also eg. n-heptoxy and n-octoxy;

$C_1–C_4$-haloalkoxy: $C_1–C_4$-alkoxy as mentioned above, which is partially or completely substituted by fluorine, chlorine and/or bromine, that is eg. chloromethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, preferably $C_1–C_2$-haloalkoxy such as trifluoromethoxy;

$C_1–C_4$-alkylthio: methylthio, ethylthio, n-propylthio, 1-methylethylthio, n-butylthio, 1-methylpropylthio, 2-methylpropylthio and 1,1-dimethylethylthio, preferably methylthio, ethylthio and methylethylthio;

$C_1–C_4$-haloalkylthio: chloromethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-fluoroethylthio, 2-fluoroethylthio, 2,2-difluoroethylthio, 2,2,2-trifluoro-ethylthio, 2-chloro-2-fluoroethylthio, 2-chlor-2,2-difluoroethylthio, 2,2-dichloro-2-fluoroethylthio, 2,2,2-trichloroethylthio and pentafluoroethylthio, preferably $C_1–C_2$-haloalkylthio such as trifluoromethylthio;

$C_3–C_6$-alkenyloxy: prop-1-en-1-yloxy, prop-2-en-1-yloxy, 1-methylethenyloxy, n-buten-1-yloxy, n-buten-2-yloxy, n-buten-3-yloxy, 1-methylprop-1-en-1-yloxy, 2-methylprop-1-en-1-yloxy, 1-methylprop-2-en-1-yloxy, 2-methylprop-2-en-1-yloxy, n-penten-1-yloxy, n-penten-2-yloxy, n-penten-3-yloxy, n-penten-4-yloxy, 1-methylbut-1-en-1-yloxy, 2-methylbut-1-en-1-yloxy, 3-methylbut-1-en-1-yloxy, 1-methylbut-2-en-1-yloxy, 2-methylbut-2-en-1-yloxy, 3-methylbut-2-en-1-yloxy, 1-methylbut-3-en-1-yloxy, 2-methylbut-3-en-1-yloxy, 3-methylbut-3-en-1-yloxy, 1,1-dimethylprop-2-en-1-yloxy, 1,2-dimethylprop-1-en-1-yloxy, 1,2-dimethylprop-2-en-1-yloxy, 1-ethylprop-1-en-2-yloxy, 1-ethylprop-2-en-1-yloxy, n-hex-1-en-1-yloxy, n-hex-2-en-1-yloxy, n-hex-3-en-1-yloxy, n-hex-4-en-1-yloxy, n-hex-5-en-1-yloxy, 1-methylpent-1-en-1-yloxy, 2-methylpent-1-en-1-yloxy, 3-methylpent-1-en-1-yloxy, 4-methylpent-1-en-1-yloxy, 1-methylpent-2-en-1-yloxy, 2-methylpent-2-en-1-yloxy, 3-methylpent-2-en-1-yloxy, 4-methylpent-2-en-1-yloxy, 1-methylpent-3-en-1-yloxy, 2-methylpent-3-en-1-yloxy, 3-methylpent-3-en-1-yloxy, 4-methylpent-3-en-1-yloxy, 1-methylpent-4-en-1-yloxy, 2-methylpent-4-en-1-yloxy, 3-methylpent-4-en-1-yloxy, 4-methylpent-4-en-1-yloxy, 1,1-dimethylbut-2-en-1-yloxy, 1,1-dimethylbut-3-en-1-yloxy, 1,2-dimethylbut-1-en-1-yloxy, 1,2-dimethylbut-2-en-1-yloxy, 1,2-dimethylbut-3-en-1-yloxy, 1,3-dimethylbut-1-en-1-yloxy, 1,3-dimethylbut-2-en-1-yloxy, 1,3-dimethylbut-3-en-1-yloxy, 2,2-dimethylbut-3-en-1-yloxy, 2,3-dimethylbut-1-en-1-yloxy, 2,3-dimethylbut-2-en-1-yloxy, 2,3-dimethylbut-3-en-1-yloxy, 3,3-dimethylbut-1-en-1-yloxy, 3,3-dimethylbut-2-en-1-yloxy, 1-ethylbut-1-en-1-yloxy, 1-ethylbut-2-en-1-yloxy, 1-ethylbut-3-en-1-yloxy, 2-ethylbut-1-en-1-yloxy, 2-ethylbut-2-en-1-yloxy, 2-ethylbut-3-en-1-yloxy, 1,1,2-trimethylprop-2-en-1-yloxy, 1-ethyl-1-methylprop-2-en-1-yloxy, 1-ethyl-2-methylprop-1-en-1-yloxy and 1-ethyl-2-methylprop-2-en-1-yloxy, preferably ethenyloxy and prop-2-en-1-yloxy;

phenoxy-$C_1–C_4$-alkyl: phenoxymethyl, 1-phenoxyethyl, 2-phenoxyethyl, 1-phenoxyprop-1-yl, 2-phenoxyprop-1-yl, 3-phenoxyprop-1-yl, 1-phenoxybut-1-yl, 2-phenoxybut-1-yl, 3-phenoxybut-1-yl, 4-phenoxybut-1-yl, 1-phenoxybut-2-yl, 2-phenoxybut-2-yl, 3-phenoxybut-2-yl, 2-phenoxybut-2-yl, 4-phenoxybut-2-yl, 1-(phenoxymethyl)eth-1-yl, 1-(phenoxymethyl)-1-(methyl)eth-1-yl and 1-(phenoxymethyl)-prop-1-yl, preferably phenoxymethyl;

$C_1–C_4$-alkylamino: methylamino, ethylamino, n-propylamino, 1-methylethylamino, n-butylamino, 1-methylpropylamino, 2-methylpropylamino and 1,1-dimethylethylamino, preferably methylamino and ethylamino;

di-($C_1$–$C_4$-alkyl)amino: N,N-dimethylamino, N,N-diethylamino, N,N-dipropylamino, N,N-di-(1-methylethyl)amino, N,N-dibutylamino, N,N-di-(1-methylpropyl)amino, N,N-di-(2-methylpropyl)amino, N,N-di-(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl) amino, N-ethyl-N-(1,1-dimethyethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl) amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino, preferably dimethylamino and diethylamino;

$C_1$–$C_4$-alkylaminocarbonyl: methylaminocarbonyl, ethylaminocarbonyl, n-propylaminocarbonyl, 1-methylethylaminocarbonyl, n-butylaminocarbonyl, 1-methylpropylaminocarbonyl, 2-methylpropylaminocarbonyl and 1,1-dimethylethylaminocarbonyl, preferably methylaminocarbonyl and ethylaminocarbonyl;

di-($C_1$–$C_4$-alkyl)aminocarbonyl: N,N-dimethylaminocarbonyl, N,N-diethylaminocarbonyl, N,N-dipropylaminocarbonyl, N,N-di-(1-methylethyl)aminocarbonyl, N,N-dibutylaminocarbonyl, N,N-di-(1-methylpropyl)aminocarbonyl, N,N-di-(2-methylpropyl)aminocarbonyl, N,N-di-(1,1-dimethylethyl)aminocarbonyl, N-ethyl-N-methylaminocarbonyl, N-methyl-N-propylaminocarbonyl, N-methyl-N-(1-methylethyl)aminocarbonyl, N-butyl-N-methylaminocarbonyl, N-methyl-N-(1-methylpropyl)aminocarbonyl, N-methyl-N-(2-methylpropyl)aminocarbonyl, N-(1,1-dimethylethyl)-N-methylaminocarbonyl, N-ethyl-N-propylaminocarbonyl, N-ethyl-N-(1-methylethyl)aminocarbonyl, N-butyl-N-ethylaminocarbonyl, N-ethyl-N-(1-methylpropyl)aminocarbonyl, N-ethyl-N-(2-methylpropyl)aminocarbonyl, N-ethyl-N-(1,1-dimethylethyl)aminocarbonyl, N-(1-methylethyl)-N-propylaminocarbonyl, N-butyl-N-propylaminocarbonyl, N-(1-methylpropyl)-N-propylaminocarbonyl, N-(2-methylpropyl)-N-propylaminocarbonyl, N-(1,1-dimethlethyl)-N-propylaminocarbonyl, N-butyl-N-(1-methylethyl) aminocarbonyl, N-(1-methylethyl)-N-(1-methylpropyl)aminocarbonyl, N-(1-methylethyl)-N-(2-methylpropyl)aminocarbonyl, N-(1,1-dimethylethyl)-N-(1-methylethyl)aminocarbonyl, N-butyl-N-(1-methylpropyl)aminocarbonyl, N-butyl-N-(2-methylpropyl)aminocarbonyl, N-butyl-N-(1,1-dimethylethyl)aminocarbonyl, N-(1-methylpropyl)-N-(2-methylpropyl)aminocarbonyl, N-(1,1-dimethylethyl)-N-(1-methylpropyl)aminocarbonyl and N-(1,1-dimethylethyl)-N-(2-methylpropyl) aminocarbonyl, preferably dimethylaminocarbonyl and diethylaminocarbonyl;

$C_1$–$C_4$-alkylsulfonyl: methylsulfonyl, ethylsulfonyl, n-propylsulfonyl, 1-methylethylsulfonyl, n-butylsulfonyl, 1-methylpropylsulfonyl, 2-methylpropylsulfonyl and 1,1-dimethylethylsulfonyl;

$C_1$–$C_4$-alkylsulfinyl: methylsulfinyl, ethylsulfinyl, n-propylsulfinyl, 1-methylethylsulfinyl, n-butylsulfinyl, 1-methylpropylsulfinyl, 2-methylpropylsulfinyl and 1,1-dimethylethylsulfinyl;

$C_1$–$C_4$-alkylsulfonylamino: methylsulfonylamino, ethylsulfonylamino, n-propylsulfonylamino, 1-methylethylsulfonylamino, n-butylsulfonylamino, 1-methylpropylsulfonylamino, 2-methylpropylsulfonylamino and 1,1-dimethylethylsulfonylamino;

$C_1$–$C_4$-haloalkylsulfonyl: $C_1$–$C_4$-alkylsulfonyl as mentioned above, which is partially or completely substituted by fluorine, chlorine and/or bromine, that is eg. chloromethylsulfonyl, dichloromethylsulfonyl, trichloromethylsulfonyl, fluoromethylsulfonyl, difluoromethylsulfonyl, trifluoromethylsulfonyl, chlorofluoromethylsulfonyl, dichlorofluoromethylsulfonyl, chlorodifluoromethylsulfonyl, 1-fluoroethylsulfonyl, 2-fluoroethysulfonyl, 2,2-difluoroethylsulfonyl, 2,2,2-trifluoroethylsulfonyl, 2-chloro-2-fluoroethylsulfonyl, 2-chloro-2,2-difluoroethylsulfonyl, 2,2-dichloro-2-fluoroethylsulfonyl, 2,2,2-trichloroethylsulfonyl and pentafluoroethylsulfonyl, preferably trichloromethylsulfonyl and trifluoromethylsulfonyl;

$C_1$–$C_4$-haloalkylsulfinyl: $C_1$–$C_4$-alkylsulfinyl as mentioned above, which is partially or completely substituted by fluorine, chlorine and/or bromine, that is eg. cloromethylsulfinyl, dichloromethylsulfinyl, trichloromethylsulfinyl, fluoromethylsulfinyl, difluoromethylsulfinyl, trifluoromethylsulfinyl, chlorofluoromethylsulfinyl, dichlorofluoromethylsulfinyl, chlorodifluoromethylsulfinyl, 1-fluoroethylsulfinyl, 2-fluoroethylsulfinyl, 2,2-difluoroethylsulfinyl, 2,2,2-trifluoroethylsulfinyl, 2,2-difluoroethylsulfinyl, 2,2,2-trifluoroethylsulfinyl, 2-chloro-2-fluoroethylsulfinyl, 2-chloro-2,2-difluoroethylsulfinyl, 2,2-dichloro-2-fluoroethylsulfinyl, 2,2,2-trichloroethylsulfinyl and pentafluoroethylsulfinyl, preferably trichloromethylsulfinyl and trifluoromethylsulfinyl;

$C_3$–$C_9$-(α-alkylalkylidene)iminooxy eg.: α-methylethylideneiminooxy and α-methylpropylideneiminooxy.

For the meanings 5- or 6-membered heteroaryl and heteroaryl-$C_1$–$C_4$-alkyl, the following heteroaromatics are suitable: 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

Suitable agriculturally utilizable cations are especially those cations which do not adversely affect the herbicidal action of the compounds I, in particular the ions of the alkali metals, preferably sodium and potassium, of the alkaline earth metals, preferably calcium, magnesium and barium, and of the transition metals, preferably manganese, copper, zinc and iron, and also the ammonium ion, which if desired can carry one to three $C_1$–$C_4$-alkyl or hydroxy-$C_1$–$C_4$-alkyl substituents and/or a phenyl or benzyl substituent, preferably diisopropylammonium, tetramethylammonium, tetrabutylammonium, trimethylbenzylammonium and trimethyl(2-hydroxyethyl)ammonium, tri($C_1$–$C_4$-alkyl)sulfonium, and sulfoxonium ions, preferably tri($C_1$–$C_4$-alkyl)sulfoxonium.

The ammonium ion and the abovementioned substituted ammonium ions are very particularly preferred cations.

The compounds I and their N-oxides are understood as meaning the following substructures Ia to Im:

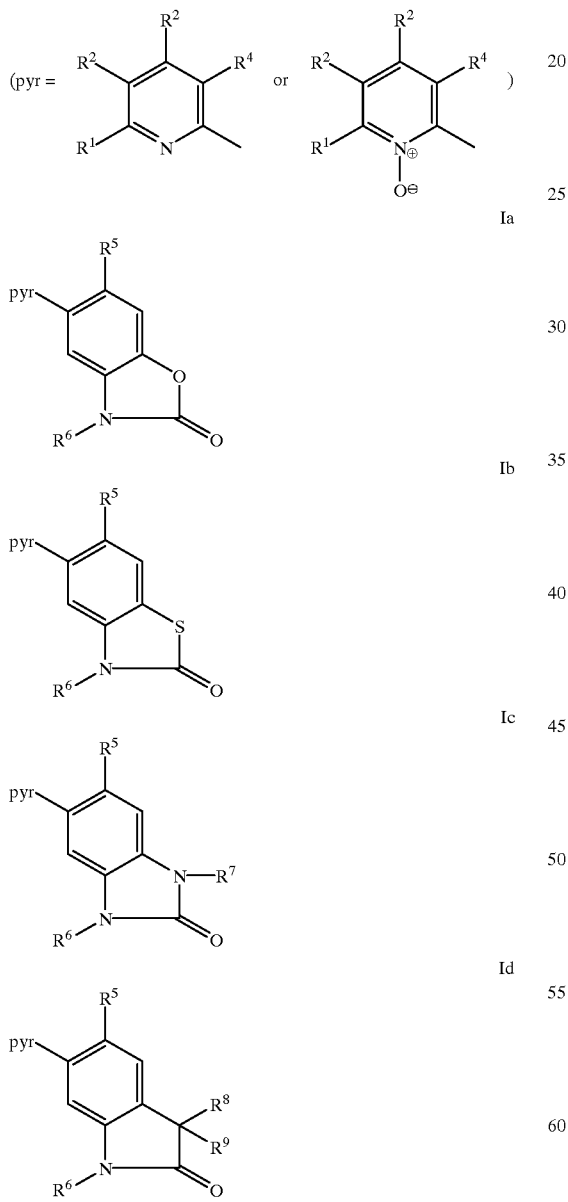

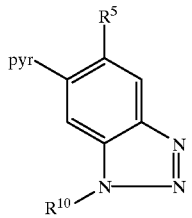

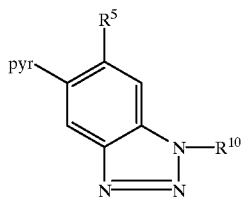

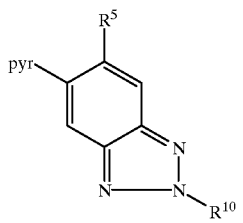

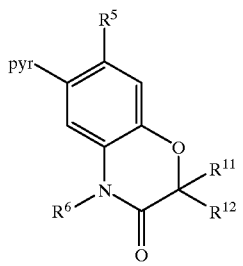

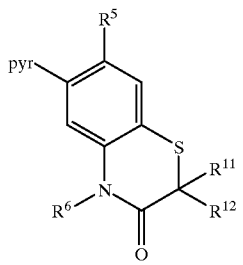

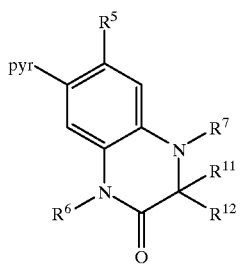

-continued

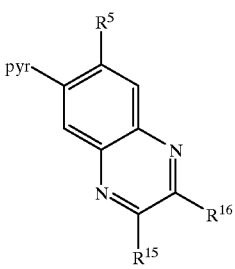

II

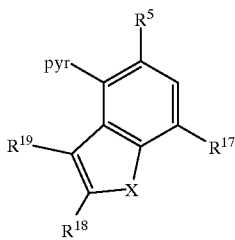

Im

The novel substituted 2-phenylpyridines I and their N-oxides are obtainable in various ways, preferably by one of the following processes:

A): Reaction of a substituted 2-halopyridine with a organometallic compound in the presence of a catalyst in an inert solvent:

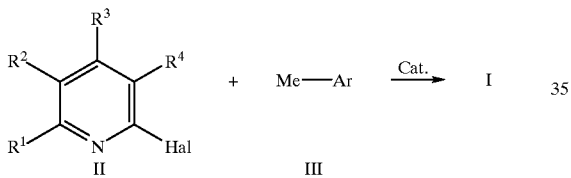

In this case Hal is chlorine or bromine, Me is Mg-Hal, Zn-Hal, tri-$C_1$–$C_4$-alkyltin, lithium, copper or B(OR$^{24}$)(OR$^{25}$), where R$^{24}$ and R$^{25}$ are hydrogen or $C_1$–$C_4$-alkyl and Cat. is a transition metal catalyst, in particular a palladium catalyst such as tetra-kis(triphenylphosphine)palladium(0), bis(1,4-diphenylphosphino)butanepalladium(II) chloride and bis(triphenylphosphine)palladium(II) chloride, or a nickel catalyst such as nickel(II) acetylacetonate, bis(triphenylphosphine)nickel(II) chloride and bis(1,3-diphenylphosphino)propanenickel(II) chloride.

Me is preferably B(OR$^{24}$)(OR$^{25}$).

Reactions of this type are generally known, for example from the following references:

Reactions with boronic acids (Me=B(OR$^{24}$)(OR$^{25}$)):
(1) W. J. Thompson and J. Gaudino, J. Org. Chem. 49 (1984) 5237;
(2) S. Gronowitz and K. Lawitz, Chem. Scr. 24 (1984) 5;
(3) S. Gronowitz et al., Chem. Scr. 26 (1986) 305;
(4) J. Stavenuiter et al., Heterocycles 26 (1987) 2711;
(5) V. Snieckus et al., Tetrahedron Letters 28 (1987) 5093;
(6) V. Snieckus et al., Tetrahedron Letters 29 (1988) 2135;
(7) M. B. Mitchell et al., Tetrahedron Letters 32 (1991) 2273; Tetrahedron 48 (1992) 8117;
(8) JP-A 93/301 870;

Reactions with Grignard compounds (Me=Mg—Hal):
(9) L. N. Pridgen, J. Heterocyclic Chem., 12 (1975) 443;
(10) M. Kumada et al., Tetrahedron Letters, 21 (1980) 845, ibid 22 (1981) 5319;
(11) A. Minato et al., J. Chem. Soc., Chem. Commun., (1984) 511;

Reactions with organozinc compounds {Me=Zn—Hal}:
(12) A. S. Bell et al., Synthesis, (1987) 843;
(13) A. S. Bell et al., Tetrahedron Letters, 29 (1988) 5013;
(14) J. W. Tilley and S. Zawoiski, J. Org. Chem. 53 (1988) 386, see also Ref. (10);

Reactions with organotin compounds {Me=Sn(alkyl)$_3$}
(15) T. R. Bailey et al., Tetrahedron Letters, 27 (1986) 4407;
(16) Y. Yamamoto et al., Synthesis, 1986, 564; see also Ref. (6).

B): For the synthesis of the substituted 2-phenylpyridines Ia and Ih, appropriate 2-(4-hydroxyphenyl)pyridines VI are expediently used as starting materials. These can be prepared in a manner known per se by electrochemical reaction of 2-halopyridines II with 2,6-di-tert-butylphenolates V and subsequent acid-catalyzed isobutene elimination (cf. eg. P. Boy et al., Synlett 1991, 923):

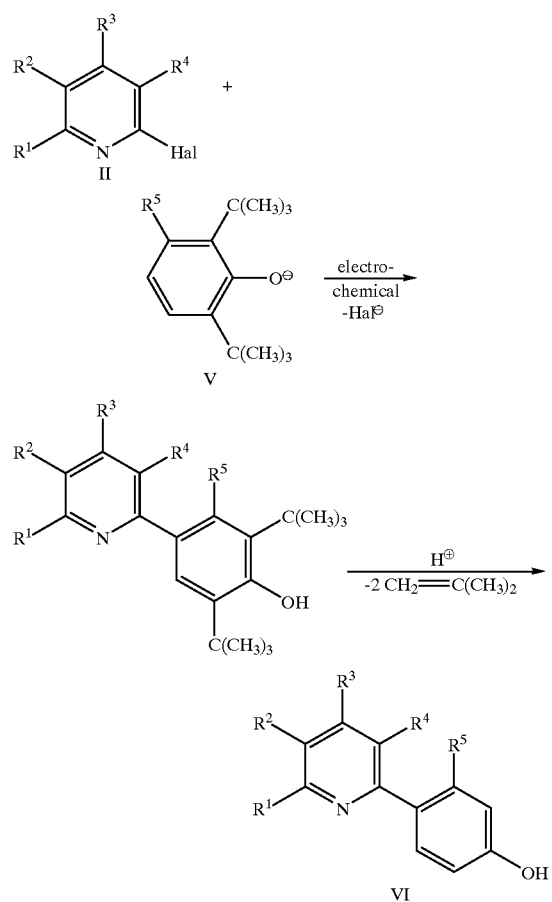

The 2-halopyridine II can also be reacted with a p-metalated phenyl-$C_1$–$C_4$-alkyl ether VII, eg. p-methoxybenzeneboronic acid. Acidic ether cleavage of the 2-(4-alkoxyphenyl)pyridine VIII, eg. with conc. aqueous hydrogen bromide solution, affords in good yield the 2-(4-hydroxyphenyl)pyridine VI:

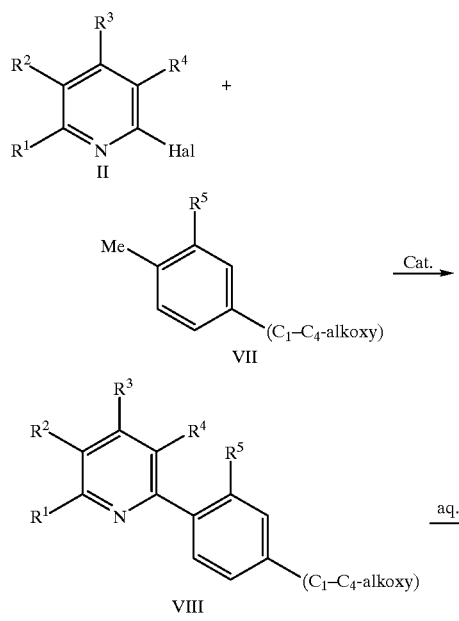

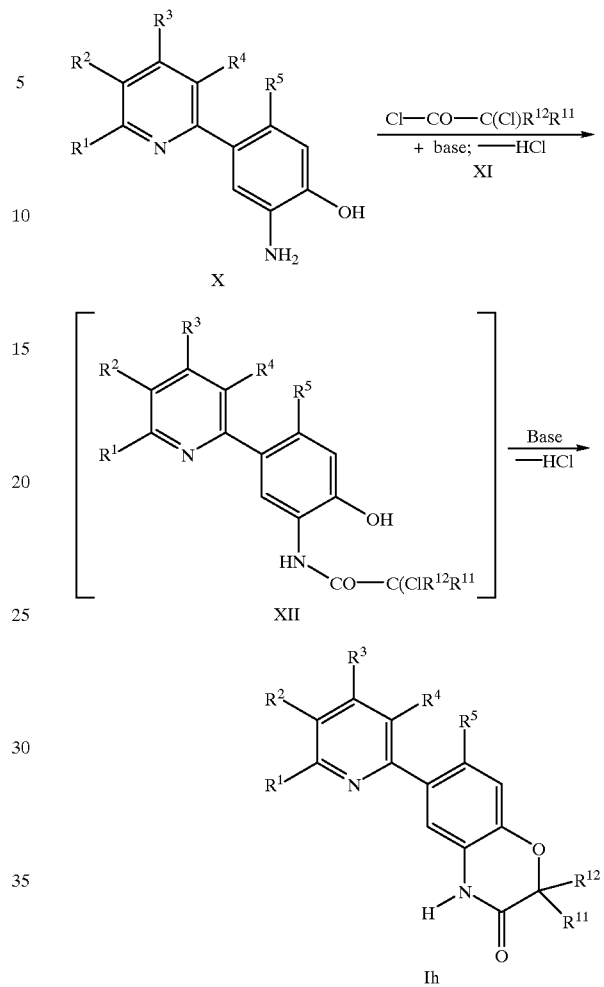

Further reaction of the 2-(4-hydroxyphenyl)pyridine VI to give the substituted 2-phenylpyridines Ia and Ih is likewise carried out by methods known from the literature, cf. eg.:

R. Tania et al., Synth. Commun. 16 (1986) 681,

EP-A 170 191,

U.S. Pat. No. 4,792,605,

EP-A 448 188.

Nitration of VI affords a 2-(4-hydroxy-5-nitrophenyl) pyridine IX whose reaction with Fe/acetic acid or $SnCl_2$/hydrochloric acid or $H_2$/cat. leads to the 2-(5-amino-4-hydroxyphenyl)pyridine X. Aclation of X with the α-chloroacid chloride XI in the presence of a base leads via the isolatable carboxanilide XII to the compound Ih (where $R^6$=hydrogen:

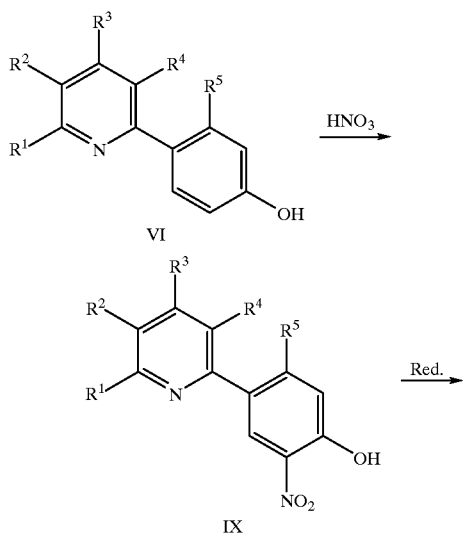

The 2-(4-hydroxy-5-nitrophenyl)pyridines of the formula IX are novel. Also novel are the 2-(5-amino-4-hydroxyphenyl)pyridines X and the carboxanilides XII which can be prepared from them.

C) The compounds Ia and Ib where $R^6$=hydrogen can likewise be prepared from the 2-(5-amino-4-hydroxyphenyl) pyridines X or from the 2-(5-amino-4-mercaptophenyl) pyridines XIII:

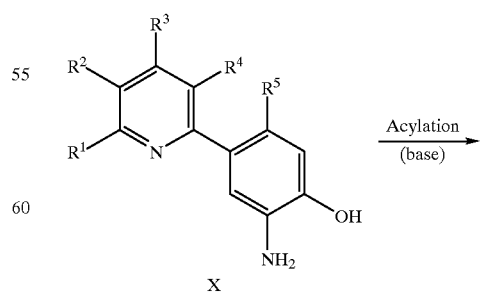

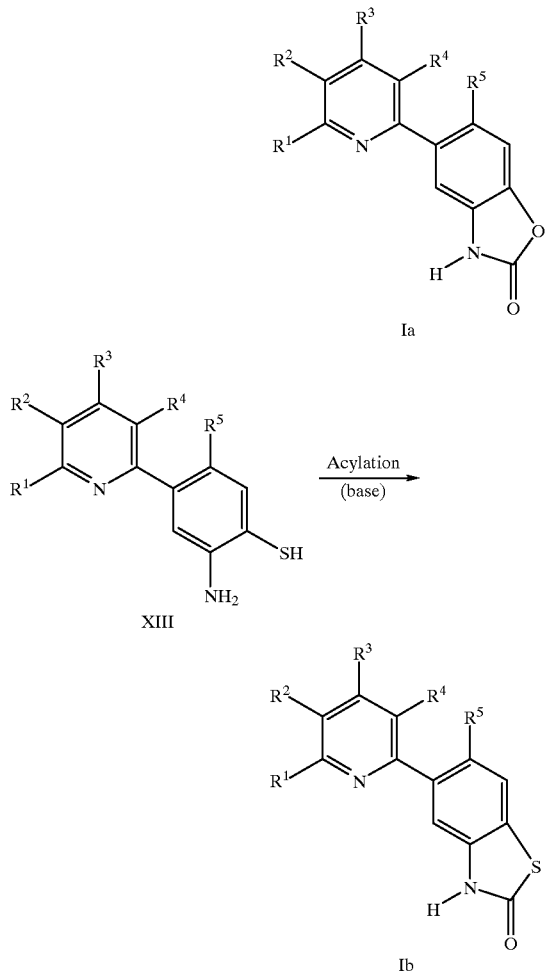

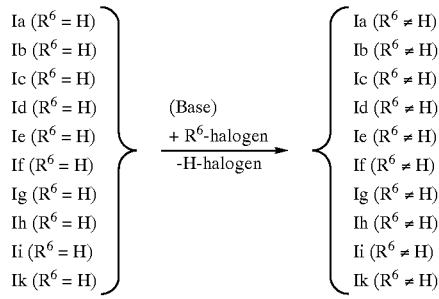

The acylation is carried out using a carbonic acid derivative such as phosgene, diphosgene, carbonyldiimidazole, chloroformic acid ester, di-2-pyridyl carbonate, disuccinimid carbonate, S,S-bis(1-phenyl-1H-tetrazol-5-yl) dithiocarbonate or urea.

The addition of a base may be advantageous, depending on the aminophenol X or aminothiophenol XIII and carbonic acid derivative employed, suitable bases in particular being inorganic salts, eg. sodium hydrogencarbonate, potassium hydrogencarbonate, sodium carbonate, potasssium carbonate, sodium hydroxide, potassium hydroxide, pyridine or tertiary amines, eg. triethylamine.

Reactions of o-aminophenols and o-aminothiophenols with carbonyl derivatives are generally known (see also J. Sam et al., J. Pharm. Sci. 58 (1969), 1043), for example from the following references:

Reaction with urea: W. J. Close et al., J. Am. Chem. Soc. 71 (1949), 1265; JP 9048 472;

Reaction with carbonyldiimidazole: R. J. Nachman, J. Heterocyclic Chem. 19 (1982), 1545;

Reaction with di-2-pyridyl carbonate: S. Kim et al., Heterocycles 24 (1986), 1625;

Reaction with S,S'-bis-(1-phenyl-1H-tetrazol-5-yl) dithiocarbonate: K. Takeda et al., Chem. Pharm. Bull. 37 (1989), 2334;

Reaction with chloroformic acid ester: R. S. Atkinson et al., J. Chem. Soc. Perkin Trans. 1981, Part 2, No. 3, p. 509;

Reaction with disuccinimido carbonate: K. Takeda et al., Synth. Commun. 12 (1982), 213;

Reaction with phosgene or diphosgene: U.S. Pat. No. 4,420,486; JP-A 60-94973; J. Weinstock et al., J. Med. Chem. 30 (1987) 1166.

D) Acylation or alkylation of the compounds Ia to Ik where $R^6$ or $R^{10}$ is hydrogen, with alkyl halides, sulfuric acid esters, carbonyl chlorides or carboxylic anhydrides leads to further compounds Ia to Ik, where $R^6$ or $R^{10}$=hydrogen. This reaction is expediently also carried out in the presence of a base:

for the acylation of benzoxazolin-2-ones with acetic anhydride see W. J. Close et al., J. Am. Chem. Soc. 71 (1949), 1265;

for the acylation of benzoxazolin-2-ones with acid chlorides see N. Cotelle et al., Synthetic Commun. 19 (1989), 3259;

for the alkylation of benzoxazolin-2-ones with alkyl halides see M. Yamato et al., Chem. and Pharm. Bull 31 (1983), 1733; U.S. Pat. No. 4,640,707; K. T. Potts et al., J. Org. Chem. 45 (1980) 4985;

for the acylation of benzothiazolin-2-ones with acetic anhydride see S. Kadoya et al., Chem. Pharm. Bull. 24 (1976), 147;

for the acylation of benzothiazolin-2-ones with acid chlorides see JP 62-201 876;

for the acylation of benzothiazolin-2-ones with chloroformic acid ester see S. Kadoya et al., Chem. and Pharm. Bull. 24 (1976), 147;

for the alkylation of benzothiazolin-2-ones with alkyl halides or sulfuric acid esters see S. Kadoya et al., Chem. and Pharm. Bull. 24 (1976), 147;

JP 62-132 873; JP 62-252 787; U.S. Pat. No. 4,720,297;

for the alkylation of benzothiazolin-2-ones by means of Michael addition to acrylic acid esters see U.S. Pat. No. 4,720,297.

E): Conversion of 3-hydroxyphenyl- or 3-mercaptophenylpyridines XIV (cf. DE-A 43 23 916) either to the propargyl ethers or propargyl thioethers XV, which are then subjected to a thermally induced or Lewis acid-catalyzed Claisen rearrangement:

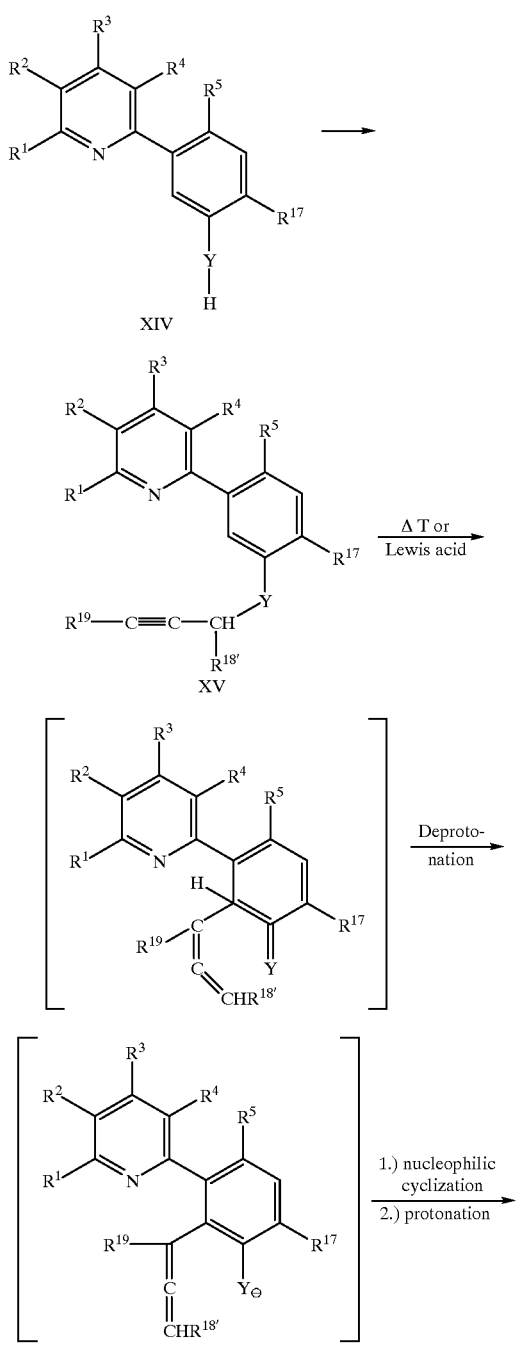

($R^{18'}$ is $C_1$–$C_5$-alkyl, $C_1$–$C_5$-haloalkyl or $C_1$–$C_4$-alkoxy-$C_1$–$C_3$-alkyl; Y is oxygen or sulfur)

or to the β-haloallyl ethers XVI, which are likewise subjected to a thermally induced or Lewis acid-catalyzed Claisen rearrangement:

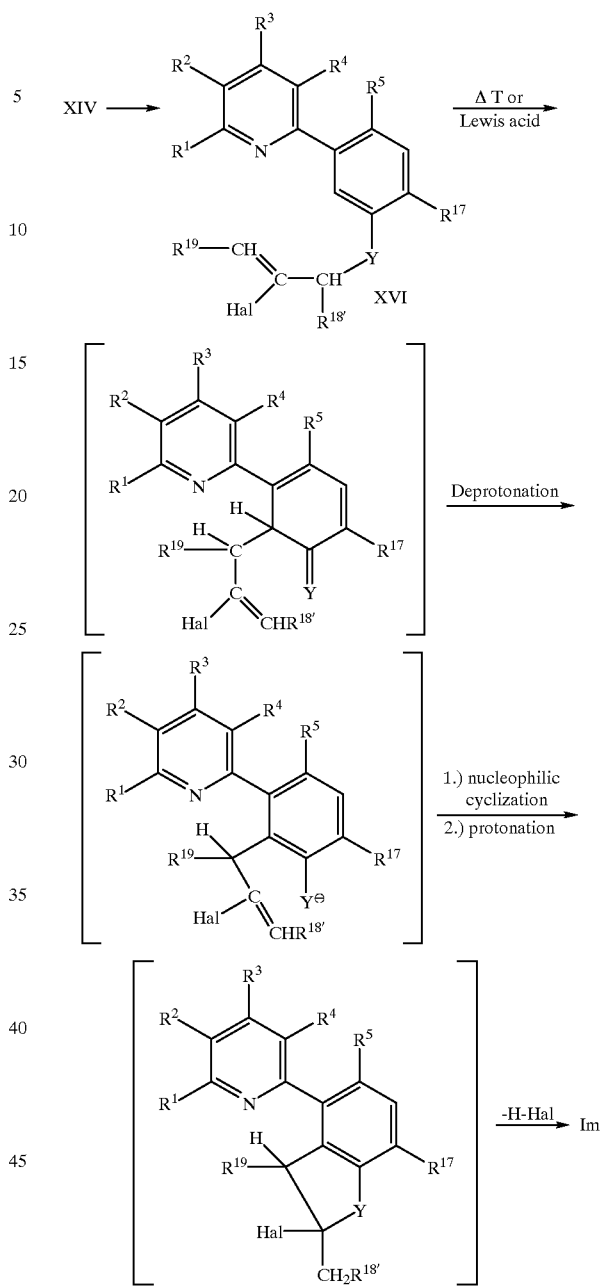

Both reactions are known in principle, eg. from EP-A 476 697. With respect to the first-mentioned variant, reference may further be made to H. Ishii et al., Chem. Pharm. Bull. 40 (1992) 1148. Reactions of the second variant are additionally known from E. K. Ryu et al., Bull Korean Chem. Soc., 13 (1992), 361.

F) Reduction of nitrophenyl derivatives XVII to the compounds Ih to Ik where $R^6$=hydrogen in a manner known per se (cf. eg. U.S. Pat. No. 4,670,042):

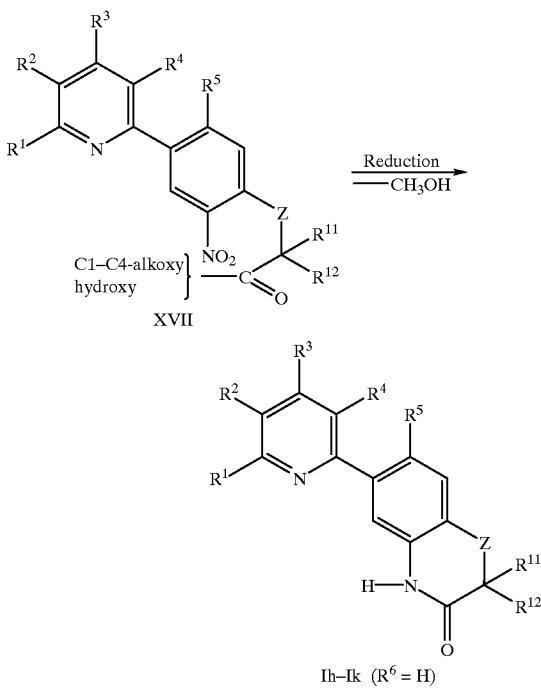

Ih–Ik (R⁶ = H)

(Z is oxygen, sulfur or N—R⁷)

Suitable reductants are, for example, hydrogen (hydrogenation on a customary catalyst) support or iron in acetic acid.

G) Reaction of diamines XVIII with halocarbonyl chlorides Cl—CO—C($R^{13}$, $R^{14}$)-halogen in a manner known per see (cf. eg. JP-A 55-49379) to give the compounds Ik where $R^6$, $R^7$=hydrogen:

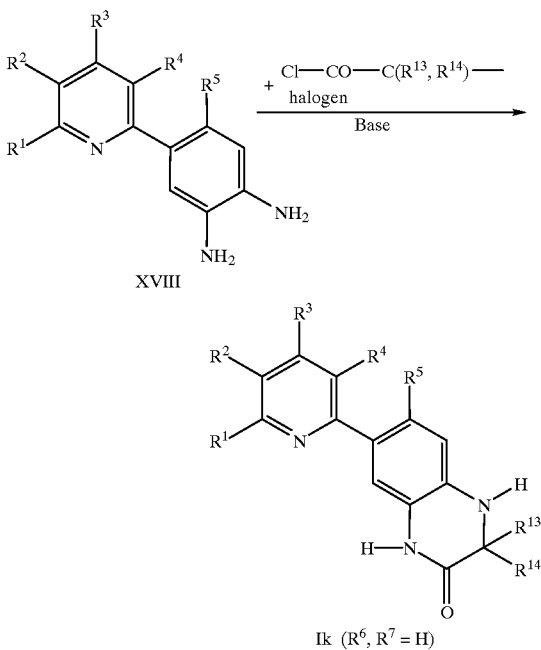

Ik ($R^6$, $R^7$ = H)

The compounds I can be converted into the N-oxides by customary methods, eg. by reaction with an organic peracid such as metachloroperbenzoic acid.

Substituted 2-phenylpyridines I where $R^1$, $R^3$ and/or $R^5$ are an alkali metal carboxylate radical can be obtained by treating compounds I where $R^1$, $R^3$ and/or $R^4$=hydroxycarbonyl eg.

with sodium hydroxide or potassium hydroxide in aqueous solution or in an organic solvent such as methanol, ethanol, acetone or toluene or with sodium hydride in an organic solvent such as dimethylformamide.

Salt formation normally takes place at an adequate rate even at about 20° C.

The salt can be isolated eg. by precipitating with a suitable inert solution or by evaporating the solvent.

Substituted 2-phenylpyridines I where $R^1$, $R^3$ and/or $R^4$ are a carboxylate radical whose counter-ion is an agriculturally utilizable cation which does not belong to the alkali metal group can customarily be prepared by double decomposition of the corresponding alkali metal carboxylates.

Compounds I where $R^1$, $R^3$ and/or $R^4$ are a carboxylate radical whose counter-ion is eg. a zinc, iron, calcium or magnesium ion can be prepared from the corresponding sodium carboxylates in the customary manner, also compounds I where $R^1$, $R^3$ and/or $R^4$ are a carboxylate radical whose counter-ion is an ammonium ion, by means of ammonia.

If not stated otherwise, all reactions described above are expediently performed at atmospheric pressure or under the autogenuous pressure of the respective reaction mixture.

The substituted 2-phenylpyridines I can be obtained during preparation as isomer mixtures which, however, can be separated if desired into the pure isomers by the methods customary for this purpose such as crystallization or chromatography, alternatively on an optically active adsorbate. Pure optically active isomers can advantageously be prepared from corresponding optically active starting materials.

The substituted 2-phenylpyridines I, their agriculturally utilizable salts and N-oxides are suitable as herbicides, both as isomer mixtures and in the form of the pure isomers. They can control broad-leaved weeds and grass weed very effectively in crops such as wheat, rice, maize, soyabeans and cotton without significantly damaging the crop plants. This effect occurs especially at low application rates.

Depending on the particular application method, the compounds I or herbicidal compositions containing them can additionally be employed in a further number of crop plants for eliminating undesired plants. Examples of suitable crops are the following:

*Allium cepa, Ananas comosus, Arachis hypogaea, Asparagus officinalis,* Beta vulgaris spp. altissima, Beta vulgaris spp. rapa, *Brassica napus var. napus, Brassica napus var. napobrassica, Brassica rapa var. silvestris, Camellia sinensis, Carthamus tinctorius, Carya illinoinensis, citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium) Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spp., *Manihot esculenta, Medicago sativa,* Musa spp., *Nicotiana tabacum (N. rustica), Olea europaea, Oryza sativa, Phaseolus lunatus, Phaseolus vulgaris, Picea abies,* Pinus spp., *Pisum sativum, Prunus avium, Prunus persica, Pyrus communis, Ribes sylvestris, Ricinus communis, Saccharum officinarum, Secale cereale, Solanum tuberosum,*

*Sorghum bicolor* (s. vulgare), *Theobroma cacao, Trifolium pratense, Triticum aestivum, Triticum durum, Vicia faba, Vitis vinifera* and *Zea mays*.

Moreover, the compounds I, their N-oxides and/or salts can be employed in crops which have been made largely resistant to the action of I by breeding and/or by means of genetic engineering methods.

In addition, the substituted 2-phenylpyridines I are also suitable for the desiccation and/or defoliation of plants. As desiccants, they are suitable in particular for the desiccation of the above-ground parts of crop plants such as potato, rape, sunflower and soybean. A completely mechanized harvesting of these important crop plants is thus made possible.

Additionally of economic interest is the facilitation of harvesting, which is made possible by the temporally concentrated dropping or reduction of the power of adhesion to the tree in the case of citrus fruits, olives or other varieties and types of pomaceous fruit, stone fruit and hard-shell dry fruit. The same mechanism, ie. the promotion of the formation of separating tissue between the fruit or leaf and stem part of the plant is also essential for a highly controllable defoliation of useful plants, in particular cotton.

Additionally, the shortening of the time interval in which the individual cotton plants become ripe leads to an enhanced fiber quality after harvesting.

The active compounds can be applied by spraying, nebulizing atomizing, scattering or watering, as such, in the form of their formulations or the application forms prepared therefrom, eg. in the form of directly sprayable solutions, powders, suspensions or dispersions, emulsions, oil dispersions, pastes, dusting compositions, scattering compositions or granules. The application forms depend entirely on the intended use; in any case if possible they should ensure the finest dispersion of the active compounds according to the invention.

The formulations are prepared in a known manner, eg. by extending the active compound with solvents and/or carriers, if desired using emulsifiers and dispersants, it also being possible to use other organic solvents as auxiliary solvents if water is used as a diluent.

Suitable inert auxiliaries for this purpose are essentially: mineral oil fractions of medium to high boiling point such as kerosene and diesel oil, and also coal tar oils and oils of vegetable or animal origin, solvents such as aromatic (eg. toluene, xylene), chlorinated aromatics (eg. chlorobenzenes), paraffins (eg. petroleum fractions), alcohols (eg. methanol, ethanol, butanol, cyclohexanol), ketones (eg. cyclohexanone, isophorone), amines (eg. ethanolamine, N,N-dimethylformamide, N-methylpyrrolidone) and water; carriers such as ground natural minerals (eg. kaolins, clays, talc, chalk) and ground synthetic minerals (eg. highly disperse silicic acid, silicates); emulsifiers such as nonionic and anionic emulsifiers (eg. polyoxyethylene fatty alcohol ethers, alkylsulfonates and arylsulfonates) and dispersants such as lignin-sulfite waste liquors and methylcellulose.

Aqueous application forms can be prepared from emulsion concentrates, dispersions, pastes, wettable powders or water-dispersible granules by addition of water. For the preparation of emulsions, pastes or oil dispersions, the substrates can be homogenized, as such or dissolved in an oil or solvent, by means of wetting agents, adhesives, dispersants or emulsifiers. However, concentrates also consisting of active substance, wetting agent, adhesive, dispersant or emulsifier and possibly solvent or oil can be prepared which are suitable for dilution with water.

Suitable surface-active substances are the alkali metal, alkaline earth metal or ammonium salts of aromatic sulfonic acids, eg. lignosulfonic acid, phenolsulfonic acid, naphthalensulfonic acid and dibutylnaphthalenesulfonic acid, and also of fatty acids, alkylsulfonates and alkylarylsulfonates, alkyl, lauryl ether and fatty alcohol sulfates, and also salts of sulfated hexa-, hepta- and octadecanols, and also of fatty alcohol glycol ethers, condensation products of sulfonated naphthalene and its derivatives with formaldehyde, condensation products of naphthalene or of napthalenesulfonic acids with phenol and formaldehyde, polyoxyethylene octyl phenol ether, ethoxylated isooctyl-, octyl- or nonlphenol, alkylphenol or tributylphenyl polyglycol ether, alkylaryl polyether alcohols, isotridecyl alcohol, fatty alcohol ethylene oxide condensates, ethoxylated castor oil, polyoxyethylene alkyl ethers or polyoxypropylene, lauryl alcohol polyglycol ether acetate, sorbitan esters, lignin-sulfite waste liquors or methylcellulose.

Powdered, scattering and dusting compositions can be prepared by mixing or joint grinding of the active substances with a solid carrier.

Granules, eg. coated, impregnated and homogeneous granules, can be prepared by binding the active compounds to solid carriers. Solid carriers are mineral earths such as silicic acids, silica gels, silicates, talc, kaolin, limestone, lime, chalk, bole, loess, clay, dolomite, diatomaceous earth, calcium sulfate and magnesium sulfate, magnesium oxide, ground plastics, fertilizers, such as ammonium sulfate, ammonium phosphate, ammonium nitrate, ureas and vegetable products, such as cereal meal, tree bark, wood and nutshell meal, cellulose powder or other solid carriers.

The concentration of the active compounds I in the ready-to-apply preparations can be varied within wide ranges, for example between 0.01 and 95% by weight.

The active compounds are in this case normally employed in a purity of 90% to 100%, preferably 95% to 100% (according to NMR spectrum).

Examples of such preparations are:

I. 20 parts of weight of the compound No. Ia.01 are dissolved in a mixture which consists of 80 parts by weight of alkylated benzene, 10 parts by weight of the addition product of from 8 to 10 mol of ethylene oxide to 1 mol of oleic acid N-mono-ethanolamide, 5 parts by weight of calcium salt of dodecylbenzenesulfonic acid and 5 parts by weight of the addition product of 40 mol of ethylene oxide to 1 mol of castor oil. By pouring out the solution and finely dispersing it in 100,000 parts by weight of water an aqueous dispersion is obtained which contains 0.02% by weight of the active compound.

II. 20 parts by weight of the compound No. Ic.01 are dissolved in a mixture which consists of 40 parts by weight of cyclohexanone, 30 parts by weight of isobutanol, 20 parts by weight of the addition product of 7 mol of ethylene oxide to 1 mol of isooctylphenol and 10 parts by weight of the addition product of 40 mol of ethylene oxide to 1 mol of castor oil. By pouring the solution into 100,000 parts by weight of water and finely dispersing it an aqueous dispersion is obtained which contains 0.02% by weight of the active compound.

III. 20 parts by weight of the active compound No. Id.01 are dissolved in a mixture which consists of 25 parts by weight of cyclohexanone, 65 parts by weight of a mineral oil fraction of boiling point 210 to 280° C. and 10 parts by weight of the addition product of 40 mol of ethylene oxide to 1 mol of castor oil. By pouring the solution into 100,000 parts by weight of water and finely dispersing it an aqueous dispersion is obtained which contains 0.02% by weight of the active compound.

IV. 20 parts by weight of the active compound No. Ig.01 are well mixed with 3 parts by weight of the sodium salt of diisobutylnaphthalene-α-sulfonic acid, 17 parts by weight of the sodium salt of a lignosulfonic acid from a sulfite wasts liquor and 60 parts by weight of powdered silicic acid gel and ground in a hammer mill. By finely dispersing the mixture in 20,000 parts by weight of water a spray liquor is obtained which contains 0.1% by weight of the active compound.

V. 3 parts by weight of the active compound No. Ih.001 are mixed with 97 parts by weight of finely divided kaolin. In this manner a dusting composition is obtained which contains 3% by weight of the active compound.

VI. 20 parts by weight of the active compound No. Im.01 are intimately mixed with 2 parts by weight of calcium salt of dodecylbenezenesulfonic acid, 8 parts by weight of fatty alcohol polyglycol ether, 2 parts by weight of sodium salt of a phenol/urea/formaldehyde condensate and 68 parts by weight of a paraffinic mineral oil. A stable oily dispersion is obtained.

The application of the active compounds or of the herbicidal and plant growth-regulating agents can be carried out pre-emergence or post-emergence. Normally, the plants are sprayed or dusted with the active compounds or the seeds of the test plants are treated with the active compounds. If the active compounds are less tolerable to certain crop plants, application techniques can be used in which the herbicidal compositions are sprayed with the aid of the spray equipment such that the leaves of the sensitive crop plants are not affected if possible, while the active compounds reach the leaves of undesired plants growing under them or the uncovered soil surface (post-directed, lay-by).

The application rate of active compound can be varied depending on the control target, time of year and growth stage. When used as herbicides or as defoliating agents, the application rate is preferably from 0.001 to 3.0, in particular from 0.01 to 1.0, kg/ha of active substance (a.s.).

To widen the spectrum of action and to achieve synergistic effects, the substituted 2-phenylpyridines I can be mixed with numerous representatives of other herbicidal or growth-regulating active compound groups and applied together. For example, suitable mixture components are diazines, 4H-3,1-benzoxazine derivatives, benzothiadiazinones, 2,6-dinitroanilines, N-phenyl-carbamates, thiocarbamates, halo-carboxylic acids, triazines, amides, ureas, diphenyl ethers, triazinones, uracils, benzofuran derivatives, cyclohexane-1, 3-dione derivatives which carry eg. a carboxyl or carbimino group in the 2-position, quinoline-carboxylic acid derivatives, imidazolinones, sulfonamides, sulfonylureas, aryloxy- or heteroaryloxyphenoxypropionic acids and their salts, esters and amides and others.

Additionally, it may be useful to apply the compounds I on their own or jointly in combination with other herbicides and additionally with other crop protection agents, for example with compositions for controlling pests or phytopathogenic fungi or bacteria. Also of interest is the miscibility with mineral salt solutions, which are employed for eliminating nutritional and trace element deficiencies. Non-phytotoxic oils and oil concentrates can also be added.

PREPARATION EXAMPLES

Example 1

6-[3-Chloro-5-trifluoromethylpyridin-2-yl]-4-propargyl-2H-1,4-benzoxazin-3-one (Table 5, Compound no. Ih.001)

Preparation was carried out according to the following reaction scheme:

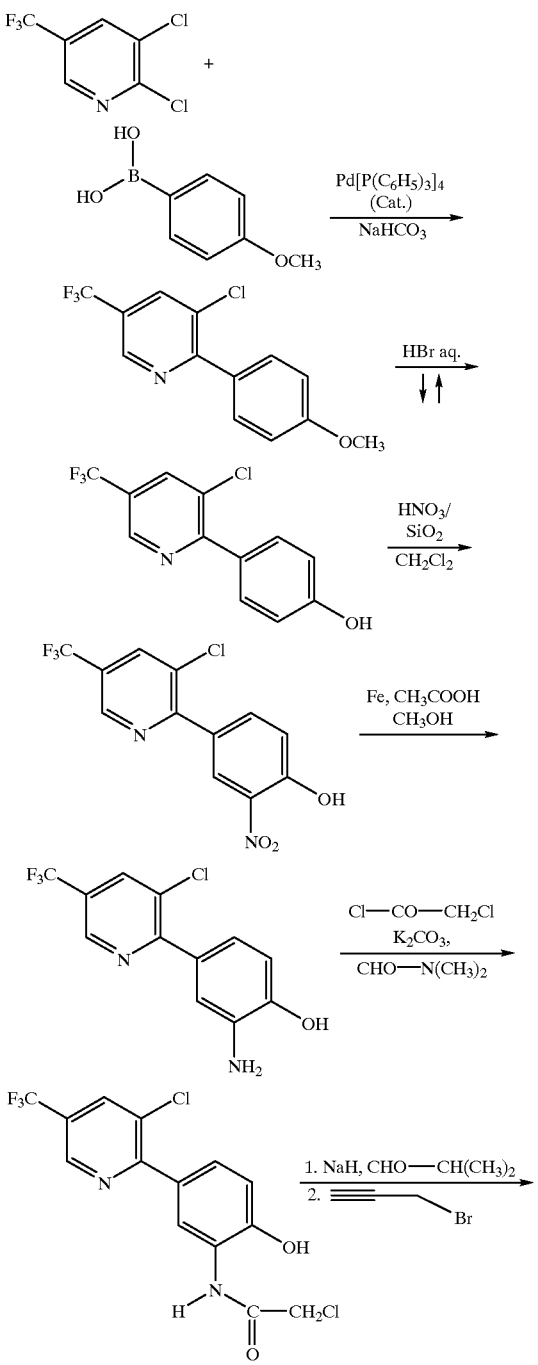

-continued

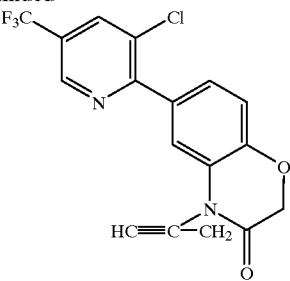

1st stage of reaction:
3-Chloro-2-(4-methoxyphenyl)-5-trifluoromethylpyridine 20.4 g of 2,3-dichloro-5-trifluoromethylpyridine, 18.9 g of p-methoxyphenylboronic acid, 0.4 g of tetrakis (triphenylphosphine)palladium(0) and 23.8 g of sodium hydrogencarbonate were refluxed for 2 hours in a mixture of 300 ml of tetrahydrofuran and 300 ml of water. After colling, the mixture was acidified by means of 10% strength hydrochloric acid. The tetrahydrofuran was removed by distillation under reduced pressure, and the product was then extracted three times with 100 m of methylene chloride in each case. The combined organic phases were sucked through silica gel and then evaporated. Recrystallization of the crude product from n-hexane gave 19.5 g (72%) of colorless crystals; m.p. 71–72° C.

2nd stage of reaction:
3-Chloro-2-(4-hydroxyphenyl)-5-trifluoromethylpyridine

A suspension of 10.0 g (34.8 mmol) of 3-chloro-2-(4-methoxyphenyl)-5-trifluoromethylpyridine in 50 ml of 47% strength hydrobromic acid was heated at reflux temperatures for two hours. After cooling, the reaction mixture was diluted with 200 ml of water. After cooling for a few hours, the resulting crystals were separated off, washed with water and dried under reduced pressure. Yield: 8.0 g (84%) of colorless crystals.

$^1$H-NMR (270 MHz, in CDCl$_3$): δ [ppm]=6.79 (d, 2 H), 6.8–7.6 (br., 1 H), 7.62 (d, 2 H), 8.08 (s, 1 H), 8.82 (s, 1 H).

3rd stage of reaction:
3-Chloro-2-(4-hydroxy-3-nitrophenyl)-5-trifluoromethylpyridine The nitration was carried out according to the working procedure of R. Tapia et al., Synth. Commun. 16 (1986) 681:

A mixture of 8.0 g (29.3 mmol) of 3-chloro-2-(4-hydroxyphenyl)-5-trifluoromethylpyridine, 7.1 g (29.3 mmol) of HNO$_3$/SiO$_2$ (HNO$_3$ content about 26%) and 200 ml of methylene chloride was stirred at 20–25° C. for about 15 hours. The SiO$_2$ was filtered off with suction and washed with methylene chloride. After evaporating the combined methylene chloride phases, the oily residue was purified by chromatography on silica gel (eluent: cyclohexane/ethyl acetate 6:1). Yield: 9.0 g (96%) of colorless crystals of m.p.: 62–63° C.

$^1$H-NMR (250 MHz, in CDCl$_3$): δ [ppm]=7.29 (d, 1 H), 8.08 (s, 1 H), 8.10 (dd, 1 H), 8.68 (d, 1 H), 8.88 (s, 1 H), 10.80 (s,br., 1 H).

4th stage of reaction:
3-Chloro-2-(3-amino-4-hydroxyphenyl)-5-trifluoromethylpyridine 6.2 g (110 mmol) of iron powder were heated to reflux temperature in a mixture of 66 ml of methanol and 33 ml of glacial acetic acid and treated in portions with a total of 11.7 g (36.7 mmol) of 3-chloro-2-(4-hydroxy-3-nitrophenyl)-5-trifluoromethylpyridine. After addition was complete. The mixture was heated for a further 2 hours at reflux temperature, allowed to cool and diluted with 130 ml of ethyl acetate. The solid components were separted off, washed with ethyl acetate and discarded. The filtrate was treated with water so that two phases were formed. The aqueous phase was separated off and extracted twice with ethyl acetate. The combined organic phases were washed with water, dried over sodium sulfate and filtered through silica gel. Yield: 7.8 g (74%) of a dark oil.

$^1$H-NMR (250 MHz, in d$^6$-dimethyl sulfoxide): δ [ppm]= 4.75 (s, br., 2 H), 6.77 (d, 1 H), 6.92 (dd, 1 H), 7.08 (d, 1 H), 8.47 (s, 1 H), 8.98 (s, 1 H), 9.65 (s, br., 1 H).

5th stage of reaction:
3-Chloro-3-[3-(2-chloroacetylamino)-4-hydroxyphenyl]-5-trifluoromethylpyridine 3.8 g (33.3 mmol) of chloroacetyl chloride were added dropwise at 0° C. to a mixture of 7.4 g (25.6 mmol) of 3-chloro-2-(3-amino-4-hydroxyphenyl)-5-trifluoromethylpyridine and 2.1 g (15.4 mmol) of potassium carbonate in 100 ml of anhydrous dimethylformamide. After stirring at 90° C. for three hours, the reaction mixture was allowed to cool and then poured into 500 ml of water. The solid portion was filtered off with suction, washed with water and dried under reduced pressure. Yield: 7.3 g (87%) of colorless crystals of m.p.: 205° C.

$^1$H-NMR (250 MHz, in d$^6$-dimethyl sulfoxide): δ [ppm]= 4.44 (s, 2 H), 7.04 (d, 1 H), 7.49 (dd, 1 H), 8.50 (m, 2 H), 9.00 (s, 1 H), 9.62 (s, 1 H), 10.67 (s, 1 H).

6th stage of reaction:
6-[3-Chloro-5-trifluoromethylpyridin-2-yl]-4-propargyl-2H-1,4-benzoxazin-3-one A solution of 3.6 g (11.0 mmol) of 3-chloro-2-[3-(2-chloroacetylamino)-4-hydroxyphenyl]-5-trifluoromethylpyridine in 50 ml of anhydrous dimethylformamide was added dropwise at 0° C. to a suspension of 0.4 g (12 mmol) of sodium hydride (80% strength in mineral oil) which had been freed of mineral oil and 50 ml of anhydrous dimethylformamide. After stirring for 15 minutes, 1.3 g (11.0 mmol) of propargyl bromide were added dropwise to this mixture. The reaction mixture was then slowly allowed to warm to about 20° C. room temperature, stirred for a further three hours and then poured into 500 ml of ice water. The aqueous phase was extracted three times with 200 ml of ethyl acetate each time. The combined organic phases were washed twice with a little water, dried over sodium sulfate and then concetrated. Chromatographic purification of the residue on silica gel (eluent: cyclohexane/ethyl acetate 4:1) gave 1.9 g (47%) of colorless crystals of m.p.: 136–137° C.

$^1$H-NMR (250 MHz, in CDCl$_3$): δ [ppm]=2.25 (t, 1 H), 4.70 (s, 2 H), 4.74 (d, 2 H), 7.13 (d, 1 H), 7.54 (dd, 1 H), 7.68 (d, 1 H), 8.07 (s, 1 H), 8.85 (s, 1 H).

Example 2

6-[3-Chloro-5-trifluoromethylpyridin-2-yl]-4-allyl-2H-1, 4-benzoxazin-3-one (Table 5, Compound no. Ih.002)

In a similar manner to the preparation of 6-[3-chloro-5-trifluoromethylpyridin-2-yl]-4-propargyl-2H-1,4-benzoxazin-3-one described above, use of 3.4 g (10.4 mmol) of 3-chloro-2-[3-(2-chloroacetylamino)-4-hydroxyphenyl]-5-trifluoromethyl-pyridine, 0.7 g (23 mmol) of 80% strength sodium hydride suspension, 1.4 g (11.4 mmol) of allyl bromide and a total of 100 ml of anhydrous dimethylformamide gave, after chromatography of the crude product on silica gel (eluent: cyclohexane/ethyl acetate 6:1), 1.5 g (39%) of colorless crystals of m.p.: 132–134° C.

$^1$H-NMR (270 MHz, in CDCl$_3$): δ [ppm]=4.57 (d, 2 H), 4.72 (s, 2 H), 5.19–5.28 (m, 2 H), 5.80–5.98 (m, 1 H), 7.10 (d, 1 H), 7.45 (d, 1 H), 7.47 (dd, 1 H), 8.04 (s, 1 H), 8.82 (s, 1 H).

Example 3

5-(3-Chloro-5-trifluoromethylpyridin-2-yl)-1-(1-methylethyl)benzimidazol-2-one (Table 3, Compound no. Ic.01)

Preparation was carried out according to the following reaction scheme:

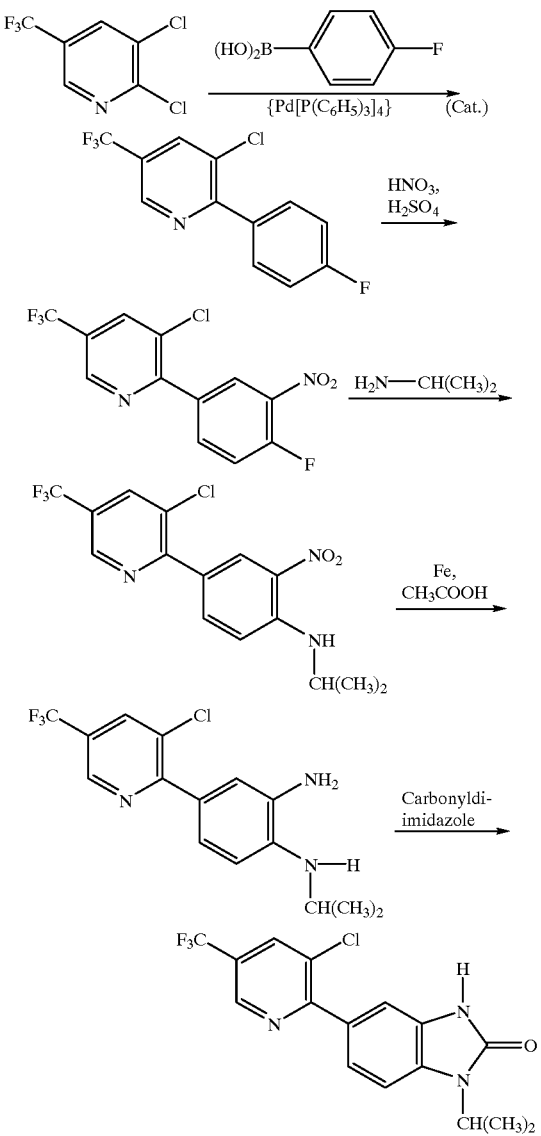

1st stage of process: 3-Chloro-2-(4-fluorophenyl)-5-trifluoromethylpyridine

In a similar manner to the preparation of 3-chloro-2-(4-methoxypenyl)-5-trifluoromethylpyridine described above, use of 55.0 g of 2,3-dichloro-5-trifluoromethylpyridine, 35.6 g of 4-fluorophenylboronic acid, 1.0 g of tetrakistriphenylphosphinepalladium, 64.2 g of sodium hydrogen carbonate, 300 ml of dimethoxyethane and 500 ml of water gave 65.0 g (93%) of colorless crystals of m.p.: 41–42° C.

2nd stage of process:
3-Chloro-2-(4-fluoro-3-nitrophenyl)-5-trifluoromethylpyridine 40.8 g of 100% nitric acid were added dropwise at from 0 to 5° C. to a solution of 118.9 g of 3-chloro-2-(4-fluorophenyl)-5-trifluoromethylpyridine in 563 ml of 96% sulfuric acid, and the mixture was then stirred at from 0 to 5° C. for 1½ hours. For work-up, the reaction mixture was poured into 2 l of ice water, and the product was then extracted with ethyl acetate (3×300 ml). The combined organic phases were washed twice with 100 ml of water in each case, dried over sodium sulfate and then evaporated. Yield: 134.5 g (97%) of a colorless oil which crystallized slowly.

$^1$H-NMR (250 MHz, in CDCl$_3$): δ[ppm]=7.47(t,1H), 8.09–8.19(m,2H), 8.60(dd,1H), 8.89(s,1H).

3rd stage of process:
3-Chloro-2-[4-(1-methylethylamino)-3-nitrophenyl]-5-trifluoromethylpyridine 44.0 g of 3-chloro-2-(4-fluoro-3-nitrophenyl)-5-trifluoromethylpyridine in 250 ml of isopropylamine were stirred at 23° C. for six hours. The reaction mixture was then concentrated. The residue was stirred with 100 ml of water, after which the residual solid portion was separated off, washed with water and dried in a vacuum drying oven. Yield: 48.2 g (98%) of colorless crystals; m.p.: 107–109° C.

4th stage of process:
2-[3-Amino-4-(1-methylethylamino)phenyl]-3-chloro-5-trifluoromethylpyridine In a similar manner to the preparation of 3-chloro-2-(3-amino-4-hydroxyphenyl)-5-trifluoromethylpyridine described above, 46.1 g of 3-chloro-2-[4-(1-methylethylamino)-3-nitro-phenyl]-5-trifluoromethylpyridine and 21.5 g of iron powder gave 39.1 g (93%) of colorless crystals; m.p.: 116–117° C.

5th stage of process:
5-(3-Chloro-5-trifluoromethylpyridin-2-yl)-1-(1-methylethyl)-benzimidazol-2-one 37.4 g of 2-[3-amino-4-(1-methylethylamino)-phenyl]-3-chloro-5-trifluoromethylpyridine and 27.6 g of carbonyldi-imidazole were heated at reflux temperature for four hours in 200 ml of anhydrous tetrahydrofuran, after which the reaction mixture was concentrated. The residue was treated with 100 ml of 10% strength hydrochloric acid and the mixture was extracted three times with 100 ml of methylene chloride each time. The combined organic phases were washed twice with 50 ml of water each time, dried over sodium sulfate and concentrated. The crude product was stirred with ether, then separated off and dried. Yield: 29.8 g (74%) of colorless crystals; m.p.: 192–193° C.

Example 4

5-(3-Chloro-5-trifluoromethylpyridin-2-yl)-3-methyl-1-(1-methylethyl)benzimidazol-2-one (Table 3, Compound No. Ic.02)

0.23 g of an 80% strength by weight suspension of sodium hydride in mineral oil was added at 23° C. to 25 ml of anhydrous dimethylformamide. The mixture was then treated dropwise with a solution of 2.50 g of 5-(3-chloro-5-trifluoromethylpyridin-2-yl)-1-(1-methylethyl)benzimidazol-2-one in 25 ml of dimethylformamide and, after stirring for 15 minutes, with 1.05 g of methyl iodide. After stirring for 6 hours, the reaction mixture was poured into 300 ml of ice water. The aqueous phase was extracted three times with 100 ml of tert-butyl methyl ether each time, after which the combined organic phases were washed twice with 50 ml of water each time, dried over sodium sulfate and concentrated. Chromatography on silica gel using cyclohexane/ethyl acetate (4:1) as the eluent gave 2.1 g of colorless crystals. Yield: 75%; m.p.: 108–109° C.

Example 5

5-(3-Chloro-5-trifluoromethylpyridin-2-yl)-1-(1-methylethyl)-3-(2-propynyl)benzimidazol-2-one (Table 3, Compound No. Ic.06)

In a similar manner to the preparation of 5-(3-chloro-5-trifluoromethylpyridin-2yl)-3-methyl-1-(1-methylethyl) benzimidazol-2-one described above, 2.5 g of 5-(3-chloro-5-trifluoromethylpyridin-2yl)-1-(1-methylethyl) benzimidazol-2-one and 0.9 g of propargyl bromide gave, after chromatography on silica gel, 1.3 g (47%) of colorless crystals. Yield: 47%; m.p.: 109–111° C.

Example 6

5-(3-Chloro-5-trifluoromethylpyridin-2-yl)-3-cyanomethyl-1-(1-methylethyl)benzimidazol-2-one (Table 3, Compound No. Ic.10)

In a similar manner to the preparation of 5-(3-chloro-5-trifluoromethylpyridin-2-yl)-3-methyl-1-(1-methylethyl) benzimidazol-2-one described above, 2.5 g of 5-(3-chloro-5-trifluoromethylpyridin-2-yl)-1-(1-methylethyl) benzimidazol-2-one and 0.9 g of bromoacetonitrile gave, after chromatography on silica gel, 1.4 g of colorless crystals. Yield: 50%; m.p.: 158–159° C.

Example 7

5-(3-Chloro-5-trifluoromethylpyridin-2-yl)-3-(2,3-epoxypropyl)-1-(1-methylethyl)benzimidazol-2-one (Table 3, Compound No. Ic.07)

In a similar manner to the preparation of 5-(3-chloro-5-trifluoromethylpyridin-2-yl)-3-methyl-1-(1-methylethyl) benzimidazol-2-one described above, 2.5 g of 5-(3-chloro-5-trifluoromethyl-pyridin-2yl)-1-(1-methylethyl) benzimidazol-2-one and 1.0 g of epibromohydrin gave 2.4 g of colorless crystals. Yield: 83%; m.p.: 110–111° C.

Example 8

5-(3-Chloro-5-trifluoromethylpyridin-2yl)-3-ethoxycarbonylmethyl-1-(1-methylethyl)benzimidazol-2-one (Table 3, Compound No. Ic08)

In a similar manner to the preparation of 5-(3-chloro-5-trifluoromethylpyridin-2yl)-3-methyl-1-(1-methylethyl) benzimidazol-2-one described above, 2.5 g of 5-(3-chloro-5-trifluoromethyl-pyridin-2yl)-1-(1-methylethyl) benzimidazol-2 -one and 1.23 g of ethyl bromoacetate gave 2.1 g (68%) of colorless crystals. Yield: 68%, m.p.L 125–127° C.

Example 9

7-(3-Chloro-5-trifluoromethylpyridin-2yl)-1,2,3,4-tetrahydro-4-methylquinoxalin-2-one (Table 7, Compound Ik.12)

Preparation was carried out according to the following reaction scheme:

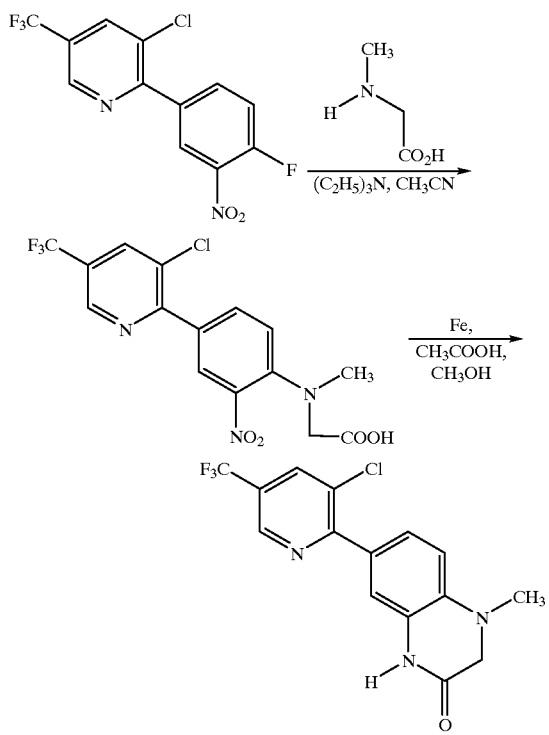

1st stage of process:
3-Chloro-2-[4-(1-hydroxycarbonylmethyl-1-methylamino)-3-nitrophenyl]-5-trifluoromethylpyridine A solution of 5.0 g of 3-chloro-2-(4-fluoro-3-nitrophenyl)-5-trifluoromethylpyridine, 1.4 g of sarcosine and 1.73 g of triethylamine in 50 ml of acetonitrile was stirred at 23° C. for 3 days and then at reflux temperature for a further four hours. The mixture was then concentrated to dryness. The residue was taken up in 100 ml of ethyl acetate, after which the organic phase was washed twice with 30 ml of water each time, dried over sodium sulfate and concentrated. The crude product was stirred in n-hexane, then filtered off and dried. Yield: 4.7 g (77%) of colorless crystals.

$^1$H-NMR (250 MHz, in d$^6$-dimethylsulfoxide): δ[ppm]= 2.90(s,3H), 4.13(s,2H), 7.20(d,1H), 7.98(dd,1H), 8.27(d, 1H), 8.58(s,1H), 9.03(s,1H), 13.0(s,1H).

2nd stage of process:
7-(3-Chloro-5-trifluoromethylpyridin-2yl)-1,2,3,4-tetrahydro-4-methylquinoxalin-2-one 3.9 g of iron powder were heated to reflux temperature in a mixture of 42 ml of methanol and 21 ml of glacial acetic acid and treated in portions with a total of 9.1 g of 3-chloro-2-[4-(1-hydroxycarbonylmethyl-1-methylamino)-3-nitrophenyl]-5-trifluoromethylpyridine. After addition was complete, the mixture was stirred for a further two hours at reflux temperature then cooled and diluted with 100 ml of ethyl acetate. The solid portion was separated off, washed with ethyl acette and discarded. The filtrate was treated with water so that two phases were formed. The aqueous phase was separated off and extracted twice with ethyl acetate. The combined organic phases were finally washed with water, dried over sodium sulfate and filtered through silica gel. Yield: 6.7 g (84%) of a colorless solid.

$^1$H-NMR (270 MHz, in CDCl$_3$): δ[ppm]=2.93(s,3H), 3.90 (s,2H), 6.74(d,1H), 7.30(d,1H), 7.53(dd,1H), 7.99(s,1H), 8.79(s,1H), 9.42(s,1H).

Example 10

7-(3-Chloro-5-trifluoromethylpyridin-2-yl)-1,2,3,4-tetrahydro-4-methyl-1-(2-propyn-1yl)quinoxalin-2-one (Table 7, Compound No. Ik.01)

A solution of 2.0 g of 7-(3-chloro-5-trifluoromethylpyridin-2yl)-1,2,3,4-tetrahydro-4-methylquinoxalin-2-one in 35 ml of dimethylformamide was added dropwise to a suspension of 0.2 g of 80% strength by weight sodium hydride in 35 ml of anhydrous dimethylformamide. After stirring for 15 minutes, 0.73 g of propargyl bromide was added to the reaction mixture. After 18 hours at 23° C., the reaction mixture was poured into 300 ml of ice water and extracted three times with 100 ml of tert-butyl methyl ether each time, after which the combined organic phases were washed twice with 100 ml of water each time, dried over sodium sulfate and concentrated. Purification of the crude product was carried out by means of chromatography on silica gel (eluent: cyclohexane/ethyl acetate). Yield: 1.1 g (49%) of colorless crystals; m.p.: 128–129° C.

Example 11

6-(3-Chloro-5-trifluoromethylpyridin-2yl)-2-isopropoxyquinoxaline and

7-(3-chloro-5-trifluoromethylpyridin-2-yl)-2-isopropoxyquinoxaline

Preparation was carried out according to the following reaction scheme:

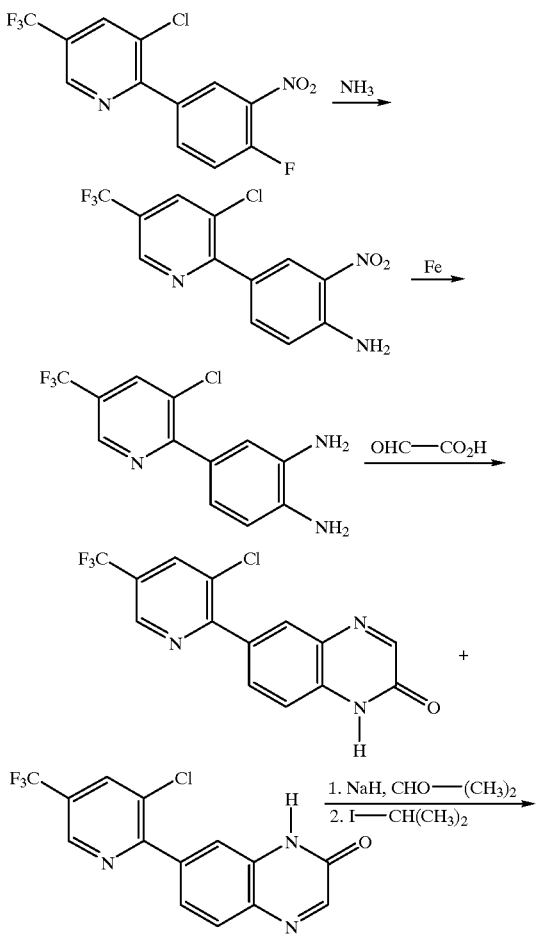

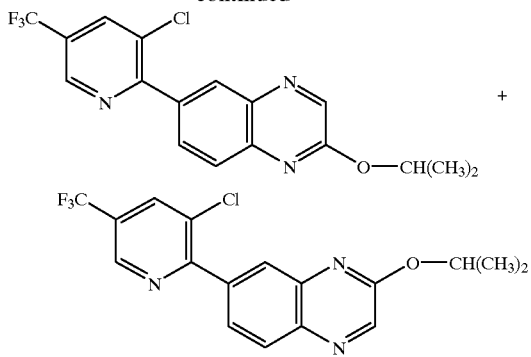

1st stage of process:

2-(4-Amino-3-nitrophenyl)-3-chloro-5-trifluoromethylpyridine

A solution of 50.0 g of 3-chloro-2-(4-fluoro-3-nitrophenyl)-5-trifluoromethylpyridine in 200 ml of tetrahydrofuran was treated with 200 g of a 25% strength by weight aqueous ammonia solution. After stirring at 23° C. for three days, the tetrahydrofuran was removed by distillation, whereupon the product crystallized. The crystals were separated off, washed with water and dried in a vacuum drying oven. Yield: 48.7 g (98%) of colorless crystals; m.p.: 126–127° C.

2nd stage of process:

2-(3,4-Diaminophenyl)-3-chloro-5-trifluoromethylpyridine

In a similar manner to the preparation of 3-chloro-2-(3-amino-4-hydroxyphenyl)-5-trifluoromethylpyridine described above, use of 48.7 g of 2-(4-amino-3-nitrophenyl)-3-chloro-5-trifluoromethylpyridine, 25.7 g of iron powder, 276 ml of methanol and 138 ml of glacial acetic acid gave, after final stirring in a little ether, 31.4 g of colorless crystals. Yield: 71%.

$^1$H-NMR (270 MHz, in $d^6$-dimethyl sulfoxide): δ[ppm]= 4.67(s,2H), 5.04(s,2H), 6.60(d,1H), 7.01(dd,1H), 7.10(d, 1H), 8.38(s,1H), 8.90(s,1H).

3rd stage of process:

6-(3-Chloro-5-trifluoromethylpyridin-2-yl)-1,2-dihydroquinoxalin-2-one and

7-(3-chloro-5-trifluoromethylpyridin-2-yl)-1,2-dihydroquinoxalin-2-one

A mixture of 10.0 g of 2-(3,4-diaminophenyl)-3-chloro-5-trifluoromethylpyridine, 5.7 g of a 50% strength by weight aqueous glyoxalic acid solution, 100 ml of ethanol and 50 ml of glacial acetic acid was stirred at 23° C. for 2.5 hours. The solid portion formed was separated off, washed with ethanol and dried. After concentrating, the filtrate gave a further amount of the products. Total yield: 87% (9.9 g of colorless crystals); isomeric ratio according to $^1$H-NMR=about 1:1).

$^1$H-NMR (270 MHz, in $^6$-dimethyl sulfoxide): δ[ppm]= 7.46(d,1H), 7.62–7.70(m,2H), 7.89–7.99(m,2H), 8.18–8.28 (m,3H), 8.62(s,1H), 8.67(s,1H), 9.07(s,1H), 9.10(s,1H),12.7 (s,2H).

4th process step:

6-(3-Chloro-5-trifluoromethylpyridin-2-yl)-2-isopropoxyquinoxaline and

7-(3-chloro-5-trifluoromethylpyridin-2-yl)-2-isopropoxyquinoxaline

A solution of 9.9 g of the mixture of 6-(3-chloro-5-trifluoromethylpyridin-2yl)-1,2-dihydroquinoxalin-2-one and 7-(3-chloro-5-trifluoromethylpyridin-2-yl)-1,2- dihydroquinoxalin-2-one obtained in the 3rd process step in 200 ml of dimethylformamide was added dropwise to suspension of 1.2 g of sodium hydride in 50 ml of dimethylformamide. After stirring for 15 minutes, 8.0 g of isopropyl iodide were added to the mixture. The reaction mixture was then stirred at 80° C. for 6 hours and at 23° C. for 64 hours. After cautious addition of 500 ml of water the mixture was extracted three times with 200 ml of tert-butyl methyl ether each time, after which the combined organic phases were washed twice with 200 ml of water each time, dried over sodium sulfate and concentrated. The residue was then chromatographed on silica gel using cyclohexane/ethyl acetate (98:2). Both products were recrystallized from n-hexane.

Fraction 1: 1.3 g of colorless crystals; m.p.: 92–93° C. $^1$H-NMR (270 MHz, in CDCl$_3$): δ[ppm]=1.45(d,6H), 5.56 (h,1H), 7.91(d,1H), 8.04–8.09(m,2H), 8.45–8.49(m,2H), 8.09(s,1H). This compound was allocated the first-mentioned structure in the heading.

Fraction 2: 0.9 g of colorless crystals; ;m.p.: 99–100° C. $^1$H-NMR (270 MHz, in CDCl$_3$): δ[ppm]=1.45(d,6H), 5.56 (h,1H), 7.92(dd,1H), 8.10–8.13(m,2H), 8.25(d,1H), 8.48(s, 1H), 8.91(s,1H). This compound was allocated the second-mentioned structure in the heading.

Example 12

5-(3-Chloro-5-trifluoromethylpyridin-2-yl)-2-ethoxycarbonyl-methylbenzotriazole (Table 12, Compound No. Ig.01), 6-(3-chloro-5-trifluoromethylpyridin-2-yl)-1-ethoxycarbonyl-methylbenzotriazole and (Table 13, Compound No. Ie.01) and 5-(3-chloro-5-trifluoromethylpyridin-2-yl)-1-ethoxycarbonyl-methylbenzotriazole (Table 11, Compound No. If.03)

Preparation was carried out according to the following reaction scheme:

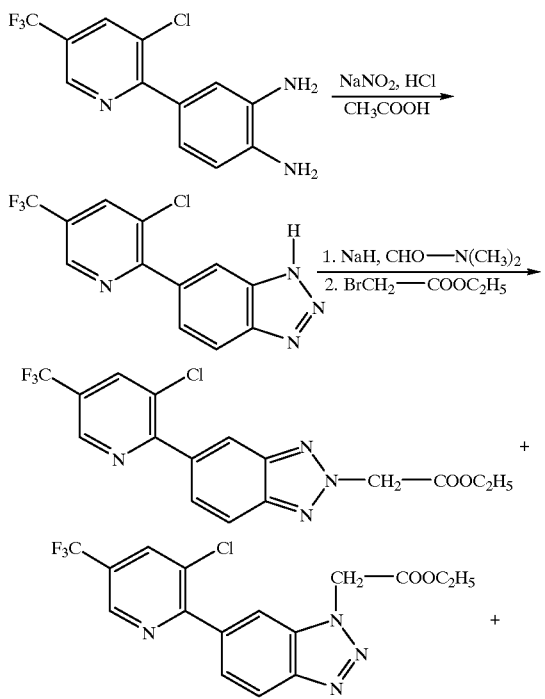

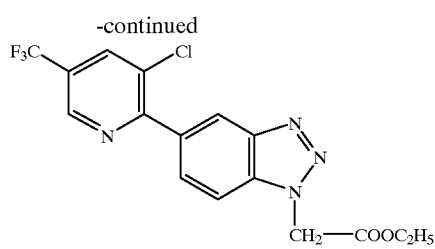

1st stage of reaction:

5-(3-Chloro-5-trifluoromethylpyridin-2-yl)benzotriazole 8 ml of concentrated hydrochloric acid and a solution of 2.64 g of sodium nitrite in 8 ml of water were added dropwise in succession with stirring and ice cooling at from 0 to 5° C. to a solution of 10.0 g of 2-(3,4-diaminophenyl)-3-chloro-5-trifluoromethylpyridine in 100 ml of glacial acetic acid. After addition was complete, the reaction mixture was allowed to warm to about 23° C., stirred for a furtehr 30 minutes and then treated with 300 ml of water. The crystals formed were separated off, washed with water and dried under reduced pressure. Yield: 8.8 g of colorless crystals.

$^1$H-NMR (270 MHz, in d$^6$-dimethyl sulfoxide): δ[ppm]= 7.80(d,1H), 8.06(d,1H), 8.34(s,1H), 8.67(s,1H), 9.08(s,1H), 16(s,br.).

2nd stage of reaction:

5-(3-Chloro-5-trifluoromethylpyridin-2-yl)-2-ethoxycarbonylmethylbenzotriazole, 6-(3-chloro-5-trifluoromethylpyridin-2-yl)-1-ethoxycarbonylmethylbenzotriazole and 5-(3-chloro-5-trifluoromethylpyridin-2-yl)-1-ethoxycarbonylmethylbenzotriazole 0.5 g of sodium hydride (80% strength by weight suspension in mineral oil) in 25 ml of anhydrous dimethylformamide was treated dropwise with a solution of 4.4 g of 5-(3-chloro-5-trifluoromethylpyridin-2-yl)benzotriazole in 25 ml of dimethylformamide. After stirring for 15 min, 2.6 g of ethyl bromoacetate were added dropwise, after which the mixture was stirred at 23° C. for 20 hours. The batch was then poured into 200 ml of water. After extracting three times with 100 ml of tert-butyl methyl ether each time, the combined organic phases were washed with 100 ml of water, dried over sodium sulfate and concentrated. The oil residue was purified by means of chromatography on silica gel (eluent: cyclohexane/ethyl acetate=6:1). The following were eluted in succession (without taking into account mixed fractions): 1.0 g of 5-(3-chloro-5-trifluoromethylpyridin-2yl)-2-ethoxycarbonylmethylbenzotriazole; m.p.: 127–129° C.

$^1$H-NMR (270 MHz, in CDCl$_3$): δ[ppm]=1.29(t,3H), 4.30 (q,2H), 5.56(s,2H), 7.79(d,$_1$H), 7.99(d,1H), 8.08(s,1H), 8.34 (s,1H), 8.88(s,1H).

1.2 g of 6-(3-chloro-5-trifluoromethylpyridin-2-yl)-1-ethoxycarbonylmethylbenzotriazole; m.p.: 107–108° C.

$^1$H-NMR (270 MHz, in CDCl$_3$): δ[ppm]=1.27(t,3H), 4.25 (q,2H), 5.48(s,2H), 7.82(d,1H), 7.93(s,1H), 8.09 (s,1H), 8.20 (d,1H), 8.89(s,1H).

1.15 g of 5-(3-chloro-5-trifluoromethylpyridin-2-yl)-1-ethoxycarbonylmethylbenzotriazole; m.p.: 123–124° C.

$^1$H-NMR (270 MHz, in CDCl$_3$); δ[ppm]=1.28(t,3H), 4.27 (q,2H), 5.47(s,2H), 7.60(d,1H), 7.95(d,1H), 8.10(s,1H), 8.57 (s,1H), 8.90(s,1H).

Example 13

6-(3-Chloro-5-trifluoromethyl-2-pyridyl)-2,3-dihydroindol-2-one (Table 4, Compound no. Id.01)

Preparation was carried out according to the following reaction scheme:

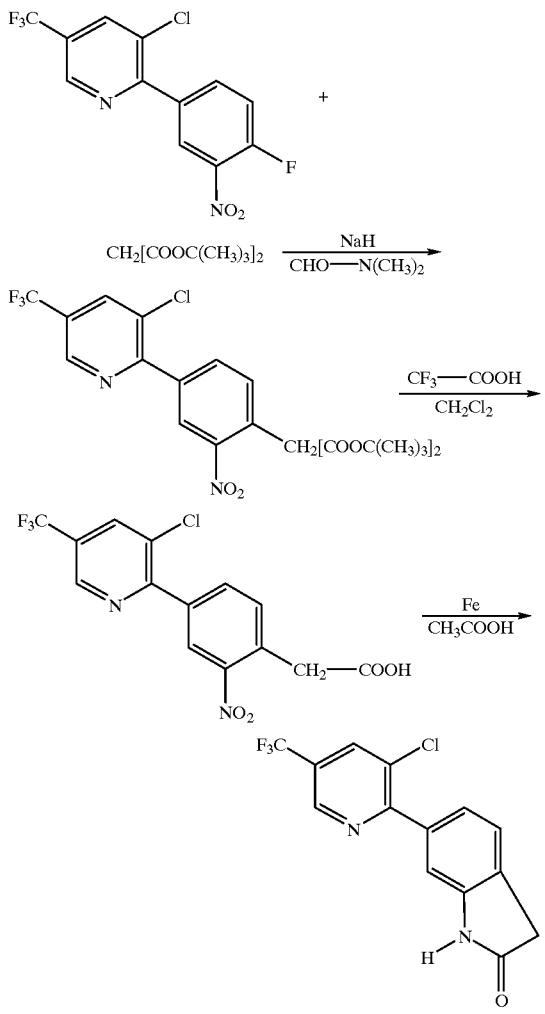

1st stage of reaction:

3-Chloro-2-[4-(bis-[1,1-dimethylethoxycarbonyl]methyl)-3-nitrophenyl]-5-trifluoromethylpyridine 0.9 g of an 80% strength by weight suspension of sodium hydride in mineral oil was added to 10 ml of anhydrous dimethylformamide. A solution of 5.1 g of di-tert-butyl malonate in 20 ml of dimethylformamide was added dropwise to this mixture, after which it was stirred for 30 minutes. A solution of 7.5 g of 3-chloro-2-(4-fluoro-3-nitrophenyl)-5-trifluoromethylpyridine in 20 ml of dimethylformamide was then added dropwise. The reaction mixture was stirred at 23° C. for 20 hours and at 80° C. for 5 hours. The cooled reaction mixture was then poured into 200 ml of ice water. The aqueous phase was extracted three times with 100 ml of tert-butyl methyl ether each time. The combined organic phases were washed with 100 ml of water, dried over sodium sulfate and concentrated. Yield: 10.8 g (79%) of a colorless oil.

$^1$H-NMR (270 MHz, in CDCl$_3$): δ [ppm]=1.51(s, 18H), 5.20(s, 1H), 7.72(d, 1H), 8.09-8.17(m, 2H), 8.56(s, 1H), 8.92(s, 1H).

2nd stage of reaction:

3-Chloro-2-(4-hydroxycarbonylmethyl-3-nitrophenyl)-5-trifluoromethylpyridine 16 ml of trifluoroacetic acid were added dropwise to a solution of 10.2 g of 3-chloro-2-[4-(bis-[1,1-dimethylethoxycarbonyl]-methyl)-3-nitrophenyl]-5-trifluoromethylpyridine in 100 ml of anhydrous dichloromethane. After stirring at 23° C. for 65 hours, the methylene chloride was removed by distillation. The residue was dissolved in 100 ml of ether, after which the ether phase was extracted three times with 50 ml of water each time, dried over sodium sulfate and concentrated. The crude product was stirred with n-hexane/ether (9:1). Yield: 5.1 g (72%) of colorless crystals.

$^1$H-NMR (270 MHz, in CDCl$_3$): δ [ppm]=4.17(s, 2H), 7.51(d, 1H), 8.07(dd, 1H), 8.13(s, 1H), 8.60(d, 1H), 8.93(s, 1H), 10.15(br., 1H).

3rd stage of reaction:

6-(3-Chloro-5-trifluoromethyl-2-pyridyl)-2,3-dihydroindol-2-one 5.1 g of 3-chloro-2-(4-hydroxycarbonylmethyl-3-nitrophenyl)-5-trifluoromethylpyridine were added in portions to a suspension of 2.4 of iron powder in a mixture of 26 ml of methanol and 13 ml of glacial acetic acid. After heating at reflux temperature for three hours, the mixture was diluted with 100 ml of ethyl acetate. The solid portion was then separated off and washed with ethyl acetate. The ethyl acetate phase was washed twice with a little water, dried over sodium sulfate and concentrated. Chromatography on silica gel using n-hexane/ethyl acetate (1:1) gave 2.85 g of a colorless oil. Yield: 64%.

$^1$H-NMR (250 MHz, in d$^6$-dimethyl sulfoxide: δ [ppm]= 3.56(s, 2H), 7.14(s, 1H), 7.32(d, 1H), 7.37(d, 1H), 8.57(s, 1H), 9.04(s, 1H), 10.55(s, 1H).

The following Tables 1 to 4 show still further compounds I which were prepared or may be prepared according to one of the processes described:

TABLE 1

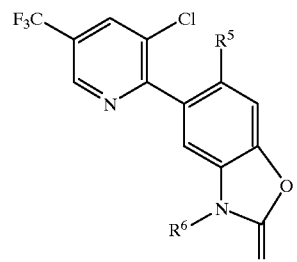

{$R^1$, $R^3$ = H; $R^2$ = CF$_3$; $R^4$ = Cl}

| No. | $R^5$ | $R^6$ | m.p.\IR [cm$^{-1}$]\ $^1$H-NMR [ppm] |
|---|---|---|---|
| Ia.01 | H | —CH$_2$—C≡C—H | 145–146° C. |
| Ia.02 | H | —CH$_2$—CH=CH$_2$ | 91–93° C. |
| Ia.03 | H | —CH(CH$_3$)—C≡C—H | |
| Ia.04 | H | —CH(CH$_3$)—CH=CH$_2$ | |
| Ia.05 | F | —CH$_2$—C≡C—H | |
| Ia.06 | F | —CH$_2$—CH=CH$_2$ | |
| Ia.07 | F | —CH(CH$_3$)—C≡C—H | |
| Ia.08 | F | —CH(CH$_3$)—CH=CH$_2$ | |
| Ia.09 | Cl | —CH$_2$—C≡C—H | |
| Ia.10 | Cl | —CH$_2$—CH=CH$_2$ | |
| Ia.11 | Cl | —CH(CH$_3$)—C≡C—H | |
| Ia.12 | H | —H | 210–212° C. |

TABLE 1-continued

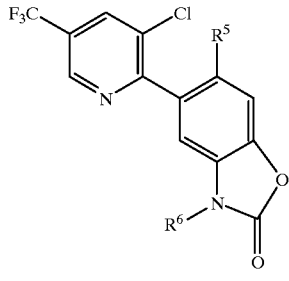

Ia

{R¹, R³ = H; R² = CF₃; R⁴ = Cl}

| No. | R⁵ | R⁶ | m.p.\IR [cm⁻¹]\ ¹H-NMR [ppm] |
|---|---|---|---|
| Ia.13 | H | —CH₃ | 171–172° C. |
| Ia.14 | H | —CH(CH₃)₂ | 1.60(d, 6H), 4.62(h, 1H), 7.33 (d, 1H), 7.56(d, 1H), 7.59(dd, 1H), 8.10(s, 1H), 8.88(s, 1H) |
| Ia.15 | H | —CH₂—CO—OC₂H₅ | 96–98° C. |
| Ia.16 | H | —CH(CH₃)—CO—OC₂H₅ | 1.25(t, 3H), 1.80(d, 3H), 4.25 (q, 2H), 5.13(q, 1H), 7.35(d, 1H), 7.43(d, 1H), 7.60(dd, 1H), 8.07(s, 1H), 8.85(s, 1H) |

TABLE 2

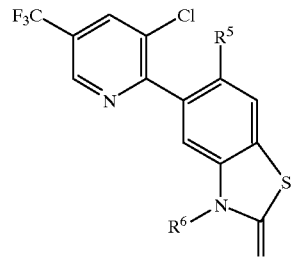

Ib

{R¹, R³ = H; R² = CF₃; R⁴ = Cl}

| No. | R⁵ | R⁶ | m.p.\IR [cm⁻¹]\ ¹H-NMR [ppm] |
|---|---|---|---|
| Ib.01 | H | —CH₂—C≡C—H | |
| Ib.02 | H | —CH₂—C≡CH₂ | |
| Ib.03 | H | —CH(CH₃)—C≡C—H | |
| Ib.04 | H | —CH(CH₃)—CH=CH₂ | |
| Ib.05 | F | —CH₂—C≡C—H | |
| Ib.06 | F | —CH₂—CH=CH₂ | |
| Ib.07 | F | —CH(CH₃)—C≡C—H | |
| Ib.08 | F | —CH(CH₃)—CH=CH₂ | |
| Ib.09 | Cl | —CH₂—C≡C—H | |
| Ib.10 | Cl | —CH₂—CH=CH₂ | |
| Ib.11 | Cl | —CH(CH₃)—C≡C—H | |

TABLE 3

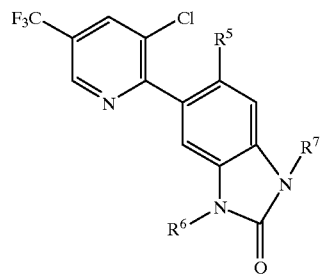

Ic

{R¹, R³ = H; R² = CF₃; R⁴ = Cl}

| No. | R⁷ | R⁶ | m.p.\IR [cm⁻¹]\ ¹H-NMR [ppm] |
|---|---|---|---|
| Ic.01 | —CH(CH₃)₂ | —H | 192–193° C. |
| Ic.02 | —CH(CH₃)₂ | —CH₃ | 108–109° C. |
| Ic.03 | —CH(CH₃)₂ | —CH₂—C₂H₅ | 74–77° C. |
| Ic.04 | —CH(CH₃)₂ | —CH(CH₃)₂ | 124–126° C. |
| Ic.05 | —CH(CH₃)₂ | —CH₂—CH=CH₂ | 85–87° C. |
| Ic.06 | —CH(CH₃)₂ | —CH₂—C≡CH | 109–111° C. |
| Ic.07 | —CH(CH₃)₂ | —CH₂—CH(O)CH₂ (epoxide) | 111° C. |
| Ic.08 | —CH(CH₃)₂ | —CH₂—CO—OC₂H₅ | 125–127° C. |
| Ic.09 | —CH(CH₃)₂ | —CH(CH₃)CO—OC₂H₅ | 1.22(t, 3H), 1.59 (d, 6H), 1.75(d, 3H), 4.21(q, 2H), 4.78 (h, 1H), 5.30(q, 1H), |

TABLE 3-continued

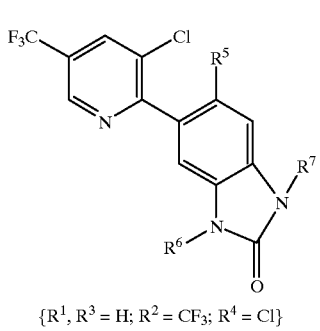

Ic

{R¹, R³ = H; R² = CF₃; R⁴ = Cl}

| No. | R⁷ | R⁶ | m.p.\IR [cm⁻¹]\ ¹H-NMR [ppm] |
|---|---|---|---|
| Ic.10 | —CH(CH₃)₂ | —CH₂—CN | 7.29(d, 1H), 7.48 (d, 1H), 7.57(dd, 1H), 8.04(s, 1H), 8.84(s, 1H) 158–159° C. |
| Ic.11 | —CH(CH₃)₂ | —CH(CH₃)—CN | 154–156° C. |
| Ic.12 | —H | —H | >300° C. in d⁶-DMSO: 7.08 (d, 1H), 7.37(d, 1H), 7.42(dd, 1H), 8.52 (d, 1H), 9.01(d, 1H), 10.83(s, 1H), 10.92 (s, 1H) |
| Ic.13 | —H | —CH₂—CO—OC₂H₅ | 241–242° C. |
| Ic.14 | —CH₃ | —CH=CH=CH₂ | 179–180° C. |
| Ic.15 | —CH₃ | —CH₂—C≡CH | 176–177° C. |
| Ic.16 | —CH₃ | —CH₂—CH=CH₂ | 147–148° C. |
| Ic.17 | —CH₃ | —CH₂—CO—OCH₃ | 185–186° C. |
| Ic.18 | —CH₃ | —CH₂—CO—OC₂H₅ | 145–146° C. |
| Ic.19 | —CH₃ | —CH(CH₃)—CO—OCH₃ | 143–144° C. |
| Ic.20 | —CH₃ | —CH(CH₃)—CO—OC₂H₅ | 106–107° C. |
| Ic.21 | —H | —CH₂—CO—OC₂H₅ | 241–242° C. |
| Ic.22 | —CH₃ | —H | 256–258° C. |
| Ic.23 | —CH₂—C≡CH | —CH₂—C≡CH | 175–177° C. |
| Ic.24 | —CH₂—CO—OC₂H₅ | —CH₂—CO—OC₂H₅ | 165–166° C. |

TABLE 4

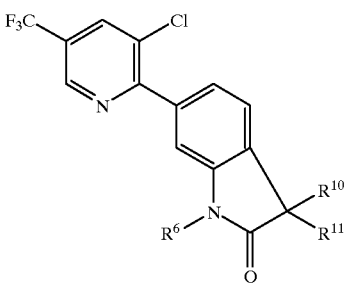

Id

{R¹, R³ = H; R² = CF₃; R⁴ = Cl}

| No. | R⁶ | R¹⁰ | R¹¹ | m.p.\IR [cm⁻¹]\ ¹H-NMR [ppm] |
|---|---|---|---|---|
| Id.01 | —H | H | H | in d⁶-DMSO: δ = 3.56(s, 2H), 7.14(s, 1H), 7.32 (d, 1H), 7.37 (d, 1H), 8.57 (s, 1H), 9.04 (s, 1H), 10.55 (s, 1H) |
| Id.02 | —CO—CH₃ | —CH₂—CH₂— | | 163–164° C. |

TABLE 4-continued

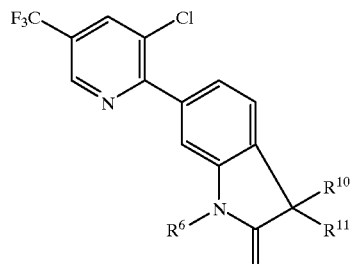

Id

{R¹, R³ = H; R² = CF₃; R⁴ = Cl}

| No. | R⁶ | R¹⁰ | R¹¹ | m.p.\IR [cm⁻¹]\ ¹H-NMR [ppm] |
|---|---|---|---|---|
| Id.03 | —H | —CH₂—CH₂— | | 1.55–1.65(m, 2H), 1.79–1.87(m, 2H), 6.93(d, 1H), 7.37 (s, 1H), 7.42 (d, 1H), 8.04 (s, 1H), 8.84 (s, 1H), 9.04 (s, 1H) |

TABLE 4-continued

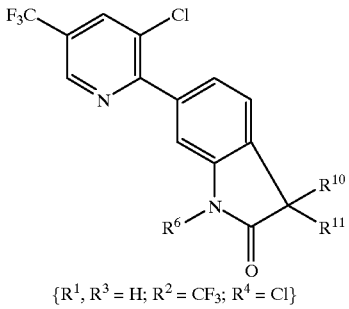

Id

{R¹, R³ = H; R² = CF₃; R⁴ = Cl}

| No. | R⁶ | R¹⁰ | R¹¹ | m.p.\IR [cm⁻¹]\ ¹H-NMR [ppm] |
|---|---|---|---|---|
| Id.04 | —CH₂—C≡CH | —CH₂—CH₂— | | 131–133° C. |

TABLE 5

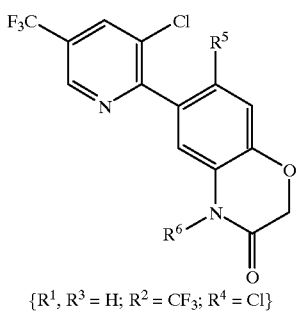

Ih

{R¹, R³ = H; R² = CF₃; R⁴ = Cl}

| No. | R⁵ | R⁶ | m.p./IR [cm⁻¹]/ ¹H-NMR [ppm] |
|---|---|---|---|
| Ih.001 | H | —CH₂—C≡C—H | 136–137° C. |
| Ih.002 | H | —CH₂—CH=CH₂ | 132–134° C. |
| Ih.003 | H | —CH(CH₃)—C≡C—H | |
| Ih.004 | H | —CH(CH₃)—CH=CH₂ | |
| Ih.005 | F | —CH₂—C≡C—H | |
| Ih.006 | F | —CH₂—CH=CH₂ | |
| Ih.007 | F | —CH(CH₃)—C≡C—H | |
| Ih.008 | F | —CH(CH₃)—CH=CH₂ | |
| Ih.009 | Cl | —CH₂—C≡C—H | |
| Ih.010 | Cl | —CH₂—CH=CH₂ | |
| Ih.011 | Cl | —CH(CH₃)—C≡C—H | |
| Ih.012 | H | —CH₂—CO—OCH₃ | 3.79(s, 3H), 4.72(s, 2H), 4.77 (s, 2H), 7.15(d, 1H), 7.23(s, 1H), 7.53(d, 1H), 8.02(s, 1H), 8.82(s, 1H); 109–110° C. |
| Ih.013 | H | —CH₂—CO—OC₂H₅ | 1.28(t, 3H), 4.24(q, 2H), 4.72 (s, 2H), 4.77(s, 2H), 7.14(d, 1H), 7.25(s, 1H), 7.52(d, 1H), 8.05(s, 1H), 8.82(s, 1H); 92–93° C. |
| Ih.014 | H | —CH(CH₃)—CO—OCH₃ | 138–139° C. |
| Ih.015 | H | —CH(CH₃)—CO—OC₂H₅ | Öl |
| Ih.016 | H | —CH₂—C₂H₅ | 1.00(t, 3H), 1.64–1.80(m, 2H), 3.94(t, 2H), 4.68(s, 2H), 7.11(d, 1H), 7.38–7.50(m, 2H), 8.04(s, 1H), 8.84(s, 1H); 93–94° C. |

TABLE 6

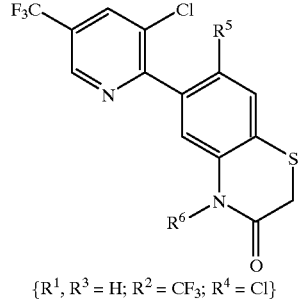

Ii

{R¹, R³ = H; R² = CF₃; R⁴ = Cl}

| No. | R⁵ | R⁶ | m.p.\IR [cm⁻¹]\¹H-NMR [ppm] |
|---|---|---|---|
| Ii.01 | H | —CH₂—C≡C—H | 159–160° C. |
| Ii.02 | H | —CH₂—CH=CH₂ | |
| Ii.03 | H | —CH(CH₃)—C≡C—H | |
| Ii.04 | H | —CH(CH₃)—CH=CH₂ | |
| Ii.05 | F | —CH₂—C≡C—H | |
| Ii.06 | F | —CH₂—CH=CH₂ | |
| Ii.07 | F | —CH(CH₃)—C≡C—H | |
| Ii.08 | F | —CH(CH₃)—CH=CH₂ | |
| Ii.09 | Cl | —CH₂—C≡C—H | |
| Ii.10 | Cl | —CH₂—CH=CH₂ | |
| Ii.11 | Cl | —CH(CH₃)—C≡C—H | |

TABLE 7

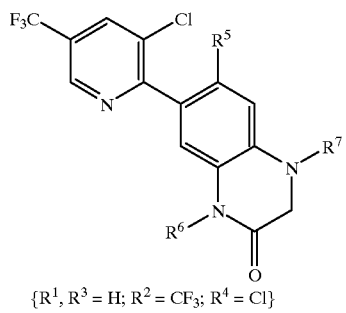

Ik

{R¹, R³ = H; R² = CF₃; R⁴ = Cl}

| No. | R⁵ | R⁷ | R⁶ | m.p.\IR [cm⁻¹]\ ¹H-NMR [ppm] |
|---|---|---|---|---|
| Ik.01 | H | CH₃ | —CH₂—C≡C—H | 128–129° C. |
| Ik.02 | H | CH₃ | —CH₂—CH=CH₂ | 234–235° C. |
| Ik.03 | H | CH₃ | —CH(CH₃)—C≡C—H | |
| Ik.04 | H | CH₃ | —CH(CH₃)—CH=CH₂ | |
| Ik.05 | F | CH₃ | —CH₂—C≡C—H | |
| Ik.06 | F | CH₃ | —CH₂—CH=CH₂ | |
| Ik.07 | F | CH₃ | —CH(CH₃)—C≡C—H | |
| Ik.08 | F | CH₃ | —CH(CH₃)—CH=CH₂ | |
| Ik.09 | H | H | —CH₂—C≡C—H | 188–190° C. |
| Ik.10 | F | H | —CH₂—C≡C—H | |
| Ik.11 | Cl | CH₃ | —CH₂—C≡C—H | |
| Ik.12 | H | CH₃ | H | 2.93(s, 3H), 3.90(s, 2H), 6.74(d, 1H), 7.30 (d, 1H), 7.53(dd, 1h), 7.99(s, 1H), 8.79(s, 1H), 9.42(s, 1H) |

TABLE 8

Ih

{R¹, R³ = H; R² = CF₃; R⁴ = Cl}

| No. | R⁶ | m.p.\IR [cm⁻¹]\ ¹H-NMR [ppm] |
|---|---|---|
| Ih.101 | —CH₂—C≡C—H | 2.29(t, 1H), 4.69(d, 2H), 4.72(s, 2H), 7.18 (s, 2H), 7.33(s, 1H), 7.62(s, 1H), 8.57 (s, 1H); 194–195° C. |

TABLE 9

Im

{R¹, R³ = H; R² = CF₃; R⁴, R¹⁷ = Cl; X = O}

| No. | R⁵ | R¹⁸ | R¹⁹ | m.p.\IR [cm⁻¹]\ ¹H-NMR [ppm] |
|---|---|---|---|---|
| Im.01 | H | H | H | 250 MHz-¹H-NMR in CDCl₃: 2.50(s, 3H), 6.43(s, 1H), 7.32 (d, 1H), 7.44(d, 1H), 8.09(s, 1H), 8.87(s, 1H) |
| Im.02 | H | CH₃ | H | |
| Im.03 | H | H | CH₃ | |
| Im.04 | H | CH₃ | CH₃ | |
| Im.05 | F | H | H | |
| Im.06 | F | CH₃ | H | |
| Im.07 | F | H | CH₃ | |
| Im.08 | F | CH₃ | CH₃ | |
| Im.09 | Cl | H | H | |
| Im.10 | Cl | CH₃ | H | |
| Im.11 | Cl | H | CH₃ | |

TABLE 10

Im

{R¹, R³ = H; R² = CF₃; R⁴, R¹⁷ = Cl; X = S}

| No. | R⁵ | R¹⁸ | R¹⁹ | m.p. or IR [cm⁻¹] or ¹H-NMR [ppm] |
|---|---|---|---|---|
| Im.12 | H | H | H | |
| Im.13 | H | CH₃ | H | |
| Im.14 | H | H | CH₃ | |
| Im.15 | H | CH₃ | CH₃ | |
| Im.16 | F | H | H | |
| Im.17 | F | CH₃ | H | |
| Im.18 | F | H | CH₃ | |
| Im.19 | F | CH₃ | CH₃ | |
| Im.20 | Cl | H | H | |
| Im.21 | Cl | CH₃ | H | |
| Im.22 | Cl | H | CH₃ | |

TABLE 11

If

{R¹, R³, R⁵ = H; R² = CF₃; R⁴ = Cl}

| No. | R¹⁰ | m.p. or IR [cm⁻¹] or ¹H-NMR [ppm] |
|---|---|---|
| If.01 | —CH(CH₃)₂ | 119–120° C. |
| If.02 | —CH₂—C₆H₅ | 176–177° C. |
| If.03 | —CH₂—CO—OC₂H₅ | 123–124° C. |

TABLE 12

Ig

{R¹, R³, R⁵ = H; R² = CF₃; R⁴ = Cl}

| No. | R¹⁰ | m.p. or IR [cm⁻¹] or ¹H-NMR [ppm] |
|---|---|---|
| Ig.01 | —CH₂—CO—OC₂H₅ | 127–129° C. |

TABLE 13

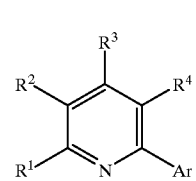

{R¹, R³, R⁵ = H; R² = CF₃; R⁴ = Cl}

| No. | R¹⁰ | m.p. or IR [cm⁻¹] or ¹H-NMR [ppm] |
|---|---|---|
| Ie.01 | —CH₂—CO—OC₂H₅ | 107–108° C. |

TABLE 14

{R¹, R³, R⁵ = H; R² = CF₃; R⁴ = Cl}

| No. | R¹⁵ | R¹⁶ | m.p. |
|---|---|---|---|
| Il.01 | —O—CH(CH₃)₂ | —H | 99–100° C. |
| Il.02 | —H | —O—CH(CH₃)₂ | 92–93° C. |

Application examples for herbicidal activity

It was possible to show the herbicidal action of the substituted 2-phenylpyridines I by means of greenhouse tests:

The cultivation containers used were plastic flower pots containing loamy sand containing about 3.0% humus as a substrate. The seeds of the test plants were sown separately according to species.

In pre-emergence treatment the active compounds suspended or emulsified in water were applied directly after sowing by means of finely dispersing nozzles. The containers were lightly sprayed to promote germination and growth, and then covered with transparent plastic hoods until the plants had taken root. This covering causes a uniform germination of the test plants if this had not been adversely affected by the active compounds.

For the purposes of post-emergence treatment, the test plants were raised, according to growth form, initially to a growth height of from 3 to 15 cm and only then treated with the active compounds suspended or emulsified in water. For this purpose, the test plants were either sown directly and cultivated in the same containers or they were first raised separately as seed plants and transplanted into the test containers a few days before the treatment. The application rate for the post-emergence treatment was 0.0625 or 0.0313 kg/has of a.s..

The plants were kept species-specifically at temperatures of 10–25° C. or 20–35° C. respectively. The test period ranged from 2 to 4 weeks. During this time the plants were tended and their reaction to the individual treatments was assessed.

Assessment was carried out according to a scale from 0 to 100. 100 here means no emergence of the plants or complete destruction at least of the above-ground parts and 0 means no damage or normal course of growth.

The plants used in the greenhouse tests consist of the following species:

| Botanical name | Common name |
|---|---|
| Abutilon theophrasti | velvet leaf |
| Ipomoea subspecies | morning glory |
| Solanum nigrum | black nightshade |
| Stellaria media | common chickweed |

At an application rate of 0.0625 or 0.0313 kg/ha, undesired broad-leaved plants can be very effectively controlled post-emergence using the compound No. Ih.001.

Application examples for growth-regulatory activity

The test plants used were young, 4-leaved (without seed leaves) cotton plants of the variety Stoneville 825, which were raised under greenhouse conditions (rel. atmospheric humidity 50 to 70%; day/night temperature 27/20° C.).

The young cotton plants were subjected to foliar treatment until dripping wet with aqueous preparations of the active compounds indicated (with addition of 0.15% by weight of the fatty alcohol alkoxylate Plurafac LF 700, based on the spray liquor). The amount of water applied was the equivalent of 1000 l/ha. After 13 days the number of shed leaves and the degree of defoliation in % was determined. No leaf fall occurred in the untreated control plants.

We claim:

1. A 2-phenylpyridine of the formula I wherein

R¹, R³ and R⁴, independently of one another, are hydrogen, halogen, $C_1$–$C_4$-alkyl, $C_1$–$C_4$-haloalkyl, $C_1$–$C_4$-alkoxy-$C_1$–$C_4$-alkyl, $C_1$–$C_4$-alkoxy, $C_1$–$C_4$-alkoxy-$C_1$–$C_4$-alkoxy, hydroxyl, $C_1$–$C_4$-haloalkoxy, ($C_1$–$C_5$-alkyl)carbonyloxy, ($C_1$–$C_5$-haloalkyl)carbonyloxy, SH, $C_1$–$C_4$-alkylthio, $C_1$–$C_4$-alkylsulfinyl, $C_1$–$C_4$-alkylsulfonyl, $C_1$–$C_4$-haloalkylthio, $C_1$–$C_4$-haloalkylsulfinyl, $C_1$–$C_4$-haloalkylsulfonyl, formyl, cyano, hydroxycarbonyl, ($C_1$–$C_4$-alkoxy)carbonyl, $C_1$–$C_4$-alkoxy-($C_1$–$C_4$-alkoxy)carbonyl, ($C_1$–$C_4$-haloalkoxy)carbonyl, ($C_1$–$C_4$-alkyl)carbonyl, ($C_1$–$C_4$-haloalkyl)carbonyl, $C_1$–$C_4$-alkoxy-($C_1$–$C_4$-alkyl)carbonyl, CONH₂, ($C_1$–$C_4$-alkyl)aminocarbonyl, di($C_1$–$C_4$-alkyl)aminocarbonyl, pyrrolidinylcarbonyl, piperidinylcarbonyl, morpholinylcarbonyl, nitro, amino, $C_1$–$C_4$-alkylamino, di($C_1$–$C_4$-alkyl)amino, pyrrolidinyl, piperidinyl, morpholinyl, ($C_1$–$C_4$-alkyl)carbonylamino, ($C_1$–$C_4$-haloalkyl)carbonylamino or $C_1$–$C_4$-alkylsulfonylamino;

R² is halogen, cyano, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, or R² and R¹ or R² and R³ form a trimethylene or a tetramethylene chain;

Ar is a bicyclic ring of the formula (h)

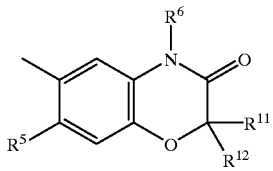

(h)

wherein

R⁵ is hydrogen or halogen;

R⁶ is hydrogen, $C_1$–$C_6$-alkyl, $C_2$–$C_6$-alkenyl, $C_2$–$C_6$-alkynyl, $C_1$–$C_6$-haloalkyl, $C_2$–$C_6$-haloalkenyl, $C_2$–$C_6$-haloalkynyl, $C_1$–$C_4$-alkoxy-$C_1$–$C_4$-alkyl, $C_1$–$C_4$-alkoxy-$C_1$–$C_2$-alkoxy-$C_1$–$C_4$-alkyl, 1-phenylpropen-3-yl, cyano-$C_1$–$C_4$-alkyl, $C_3$–$C_6$-cycloalkyl, $C_1$–$C_6$-alkyl, (1-methylthiocycloprop-1-yl)methyl, carboxyl-$C_1$–$C_4$-alkyl, ($C_1$–$C_6$-alkoxy)carbonyl-$C_1$–$C_4$-alkyl, ($C_1$–$C_6$-haloalkoxy)carbonyl-$C_1$–$C_4$-alkyl, $C_1$–$C_4$-alkoxy-($C_1$–$C_2$-alkoxy)carbonyl-$C_1$–$C_4$-alkyl, ($C_1$–$C_6$-alkoxy)carbonyl-($C_1$–$C_2$-alkoxy)carbonyl-$C_1$–$C_4$-alkyl, $C_3$–$C_6$-cycloalkyl-($C_1$–$C_2$-alkoxy)carbonyl-$C_1$–$C_4$-alkyl, $C_1$–$C_5$-alkylaminocarbonyl-$C_1$–$C_4$-alkyl, di($C_1$–$C_5$-alkyl)aminocarbonyl-$C_1$–$C_4$-alkyl, $C_3$–$C_6$-cycloalkyl, $C_1$–$C_4$-alkylthio-$C_1$–$C_4$-alkyl, $C_1$–$C_4$-alkylsulfonyl, $C_3$–$C_6$-alkenyloxy-$C_1$–$C_4$-alkyl, $C_1$–$C_8$-alkylcarbonyl, $C_1$–$C_8$-alkoxycarbonyl, $C_1$–$C_6$-alkoxy, oxetan-3-yloxycarbonyl-$C_1$–$C_4$-alkyl, thietan-3-yloxycarbonyl-$C_1$–$C_4$-alkyl, oxetan-3-ylmethyl, 3-($C_1$–$C_4$-alkyl)-oxetan-3-ylmethyl or benzyl, which is unsubstituted or carries one to three radicals selected from the group consisting of: halogen, $C_1$–$C_4$-alkyl and $C_1$–$C_4$-alkoxy;

R¹¹ and R¹², independently of one another, are hydrogen, halogen, $C_1$–$C_6$-alkyl, $C_1$–$C_6$-haloalkyl or $C_1$–$C_4$-alkoxy-$C_1$–$C_4$-alkyl, or an N-oxide of I or an agriculturally utilizable salt of I.

2. The 2-phenylpyridine of the formula I as defined in claim 1, wherein

R¹ and R³, independently of one another, are hydrogen or halogen;

R² is halogen or $C_1$–$C_4$-haloalkyl;

R⁴ is chlorine;

R⁵ is hydrogen, fluorine or chlorine;

R⁶ is hydrogen, $C_1$–$C_6$-alkyl, $C_2$–$C_6$-alkenyl, $C_2$–$C_6$-alkynyl or ($C_1$–$C_6$-alkoxy)carbonyl-$C_1$–$C_4$-alkyl;

R¹¹ and R¹², independently of one another, are hydrogen or $C_1$–$C_6$-alkyl, or an N-oxide or an agriculturally utilizable salt of I.

3. A herbicidal composition comprising a herbicidally effective amount of a 2-phenylpyridine of the formula I as defined in claim 1 or an N-oxide or an agriculturally utilizable salt thereof, and an inert liquid or solid carrier, and optionally an adjuvant.

4. A process for controlling undesired plant growth, which comprises allowing a herbicidally effective amount of a 2-phenylpyridine of the formula I as defined in claim 1 or an N-oxide or an agriculturally utilizable salt thereof, to act on plants, their environment or on seeds.

5. A process for preparing a 2-phenylpyridine of the formula I as defined in claim 1, which comprises reacting a 2-halopyridine of the formula II

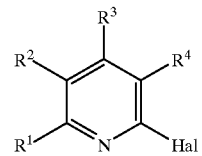

(II)

wherein Hal denotes chlorine or bromine, in the presence of a transition metal catalyst with an organometallic compound of the formula III Me—Ar   (III)

wherein Me denotes magnesium halogenid, zinc halogenid, tine tri($C_1$–$C_4$-alkyl), lithium, copper or B(OR²⁴)(OR²⁵), where R²⁴ and R²⁵, independently of one another, are hydrogen or $C_1$–$C_4$-alkyl, or where R²⁴ and R²⁵ together are ethylene or propylene.

6. The process of claim 5, wherein Me is B(OR²⁴)(OR²⁵), and R²⁴ and R²⁵ are each hydrogen.

* * * * *

UNITED STATES PATENT AND TRADEMARK OFFICE
CERTIFICATE OF CORRECTION

PATENT NO.: 6,165,941

DATED: December 26, 2000

INVENTOR(S): SCHAEFER et al.

It is certified that error appears in the above-identified patent and that said Letters Patent is hereby corrected as shown below:

Col. 51, claim 1, line 20, "cycloalkyl, $C_1$" should be --cycloalkyl-$C_1$--.

Col. 51, claim 1, line 28, "C $_1$-$C_4$-alkyl" should be --$C_1$-$C_4$-alkyl--.

Col. 52, claim 5, line 39, "tine" should be --tin,--.

Signed and Sealed this

First Day of May, 2001

Attest:

NICHOLAS P. GODICI

Attesting Officer     Acting Director of the United States Patent and Trademark Office